(12) United States Patent
Meehan et al.

(10) Patent No.: US 8,298,180 B2
(45) Date of Patent: Oct. 30, 2012

(54) SAFETY NEEDLE GUARD

(75) Inventors: Michael Meehan, Glen Rock, NJ (US); Christina D' Arrigo, Hoboken, NJ (US); Andrew Wong, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 83 days.

(21) Appl. No.: 12/275,604

(22) Filed: Nov. 21, 2008

(65) Prior Publication Data

US 2009/0216201 A1    Aug. 27, 2009

Related U.S. Application Data

(60) Provisional application No. 60/989,544, filed on Nov. 21, 2007.

(51) Int. Cl.
*A61M 5/00* (2006.01)

(52) U.S. Cl. .................. 604/110; 604/164.08; 604/192; 604/263

(58) Field of Classification Search .................. 604/110, 604/162, 163, 164.08, 192, 198, 199, 263
See application file for complete search history.

(56) References Cited

U.S. PATENT DOCUMENTS

| | | |
|---|---|---|
| 3,175,554 A | 3/1965 | Stewart |
| 3,515,137 A | 6/1970 | Santomieri |
| 4,405,307 A | 9/1983 | Taylor |
| 4,565,545 A | 1/1986 | Suzuki |
| 4,588,398 A | 5/1986 | Daugherty et al. |
| 4,609,370 A | 9/1986 | Morrison |
| 4,721,506 A | 1/1988 | Teves |
| 4,755,170 A | 7/1988 | Golden |
| 4,778,453 A | 10/1988 | Lopez |
| 4,790,828 A | 12/1988 | Dombrowski et al. |
| 4,795,432 A | 1/1989 | Karczmer |
| 4,799,495 A | 1/1989 | Hawkins et al. |
| 4,804,371 A | 2/1989 | Vaillancourt |
| 4,846,811 A | 7/1989 | Vanderhoof |
| 4,863,439 A | 9/1989 | Sanderson |
| 4,869,259 A | 9/1989 | Elkins |
| 4,929,241 A | 5/1990 | Kulli |

(Continued)

FOREIGN PATENT DOCUMENTS

EP    1752179 A2    2/2007

(Continued)

OTHER PUBLICATIONS

U.S. Appl. No. 12/275,570, filed Nov. 21, 2008, Wong.

(Continued)

*Primary Examiner* — Bhisma Mehta
(74) *Attorney, Agent, or Firm* — The Webb Law Firm

(57) ABSTRACT

A needle guard is disclosed. The needle guard includes a binding plate defining a multi-slot aperture adapted to receive a needle cannula therethrough. The needle guard also includes a biasing member for biasing the needle cannula within the multi-slot aperture, and a sensing arm connected to the binding plate. The sensing arm is adapted to contact a portion of the needle cannula, and is positionable for restricting movement of the needle cannula. The multi-slot aperture may include a first region having a first dimension, a second region having a second dimension, and optionally, a third region having a third dimension with the third dimension being smaller than the second dimension and the second dimension being smaller than the first dimension.

36 Claims, 27 Drawing Sheets

U.S. PATENT DOCUMENTS

| | | | |
|---|---|---|---|
| 4,931,048 A | 6/1990 | Lopez | |
| 4,944,725 A | 7/1990 | McDonald | |
| 4,952,207 A | 8/1990 | Lemieux | |
| 4,955,866 A | 9/1990 | Corey | |
| 4,964,854 A | 10/1990 | Luther | |
| 4,966,583 A | 10/1990 | Debbas | |
| 5,009,642 A | 4/1991 | Sahi | |
| 5,013,305 A | 5/1991 | Opie et al. | |
| 5,015,242 A | 5/1991 | Heifetz | |
| 5,049,136 A | 9/1991 | Johnson | |
| 5,053,017 A | 10/1991 | Chamuel | |
| 5,059,180 A | 10/1991 | McLees | |
| 5,106,376 A | 4/1992 | Mononen et al. | |
| 5,120,317 A | 6/1992 | Luther | |
| 5,120,321 A | 6/1992 | Oksman et al. | |
| 5,135,504 A | 8/1992 | McLees | |
| 5,141,497 A | 8/1992 | Erskine | |
| 5,147,327 A | 9/1992 | Johnson | |
| 5,149,324 A | 9/1992 | Clawson | |
| 5,171,229 A | 12/1992 | McNeil et al. | |
| 5,176,655 A | 1/1993 | McCormick et al. | |
| 5,183,468 A | 2/1993 | McLees | |
| 5,186,712 A | 2/1993 | Kelso et al. | |
| 5,217,438 A | 6/1993 | Davis et al. | |
| RE34,416 E | 10/1993 | Lemieux | |
| 5,263,936 A | 11/1993 | Yurino | |
| 5,279,570 A | 1/1994 | Dombrowski et al. | |
| 5,295,963 A | 3/1994 | Deeks | |
| 5,295,974 A | 3/1994 | O'Laughlin | |
| 5,300,045 A | 4/1994 | Plassche, Jr. | |
| 5,304,151 A | 4/1994 | Kuracina | |
| 5,314,503 A | 5/1994 | Bobrove et al. | |
| 5,322,517 A | 6/1994 | Sircom et al. | |
| 5,328,482 A | 7/1994 | Sircom et al. | |
| 5,330,432 A | 7/1994 | Yoon | |
| 5,334,158 A | 8/1994 | McLees | |
| 5,334,161 A | 8/1994 | Gurmarnik | |
| 5,336,176 A | 8/1994 | Yoon | |
| 5,336,191 A | 8/1994 | Davis et al. | |
| 5,344,408 A | 9/1994 | Partika | |
| 5,385,561 A | 1/1995 | Cerny | |
| 5,401,247 A | 3/1995 | Yoon | |
| 5,419,766 A | 5/1995 | Chang et al. | |
| 5,425,720 A | 6/1995 | Rogalsky et al. | |
| 5,425,721 A | 6/1995 | Malenchek | |
| 5,433,711 A | 7/1995 | Balaban et al. | |
| 5,458,658 A | 10/1995 | Sircom | |
| 5,466,225 A | 11/1995 | Davis et al. | |
| 5,484,423 A | 1/1996 | Waskönig et al. | |
| 5,501,672 A | 3/1996 | Firth et al. | |
| 5,533,974 A | 7/1996 | Gaba | |
| 5,533,975 A | 7/1996 | Lu | |
| 5,549,570 A | 8/1996 | Rogalsky | |
| 5,558,651 A | 9/1996 | Crawford et al. | |
| 5,562,633 A | 10/1996 | Wozencroft | |
| 5,569,217 A | 10/1996 | Luther | |
| 5,571,091 A | 11/1996 | Davis et al. | |
| 5,584,809 A | 12/1996 | Gaba | |
| 5,584,818 A | 12/1996 | Morrison | |
| 5,599,310 A | 2/1997 | Bogert | |
| 5,601,532 A | 2/1997 | Gaba | |
| 5,611,781 A | 3/1997 | Sircom et al. | |
| 5,630,802 A | 5/1997 | Moellmann et al. | |
| 5,662,610 A | 9/1997 | Sircom | |
| 5,683,365 A | 11/1997 | Brown et al. | |
| 5,683,368 A | 11/1997 | Schmidt | |
| 5,683,370 A | 11/1997 | Luther et al. | |
| 5,697,907 A | 12/1997 | Gaba | |
| 5,718,688 A | 2/1998 | Wozencroft | |
| 5,725,504 A | 3/1998 | Collins | |
| 5,741,233 A | 4/1998 | Riddle et al. | |
| 5,743,882 A | 4/1998 | Luther | |
| 5,743,888 A | 4/1998 | Wilkes et al. | |
| 5,743,891 A | 4/1998 | Tolkoff et al. | |
| 5,746,718 A | 5/1998 | Steyn | |
| 5,755,699 A | 5/1998 | Blecher et al. | |
| 5,817,060 A | 10/1998 | Overton et al. | |
| 5,833,670 A | 11/1998 | Dillon et al. | |
| 5,846,226 A | 12/1998 | Urmey | |
| 5,853,393 A | 12/1998 | Bogert | |
| 5,879,337 A | 3/1999 | Kuracina et al. | |
| 5,882,337 A | 3/1999 | Bogert et al. | |
| 5,891,093 A | 4/1999 | Dysarz | |
| 5,910,132 A | 6/1999 | Schultz | |
| 5,913,848 A | 6/1999 | Luther et al. | |
| 5,916,208 A | 6/1999 | Luther et al. | |
| 5,951,529 A | 9/1999 | Utterberg | |
| 6,001,080 A | 12/1999 | Kuracina et al. | |
| 6,004,294 A | 12/1999 | Brimhall et al. | |
| 6,080,135 A | 6/2000 | Van Stokkum | |
| RE36,885 E | 9/2000 | Blecher et al. | |
| 6,117,108 A | 9/2000 | Woehr et al. | |
| 6,120,480 A | 9/2000 | Zhang et al. | |
| 6,132,402 A | 10/2000 | Tessmann et al. | |
| 6,165,157 A | 12/2000 | Dillon et al. | |
| 6,203,527 B1 | 3/2001 | Zadini et al. | |
| 6,210,372 B1 | 4/2001 | Tessmann et al. | |
| 6,210,373 B1 | 4/2001 | Allmon | |
| 6,221,047 B1 | 4/2001 | Greene et al. | |
| 6,235,001 B1 | 5/2001 | O'Holloran et al. | |
| 6,235,006 B1 | 5/2001 | Dillon et al. | |
| 6,280,419 B1 | 8/2001 | Vojtasek | |
| 6,287,278 B1 | 9/2001 | Woehr et al. | |
| 6,322,537 B1 | 11/2001 | Chang | |
| 6,379,332 B1 | 4/2002 | Van Landuyt | |
| 6,379,333 B1 | 4/2002 | Brimhall et al. | |
| 6,406,459 B1 | 6/2002 | Allmon | |
| 6,443,927 B1 | 9/2002 | Cook | |
| 6,443,929 B1 | 9/2002 | Kuracina et al. | |
| 6,475,189 B1 | 11/2002 | Lilley, Jr. | |
| 6,485,468 B2 | 11/2002 | Vojtasek | |
| 6,500,153 B1 | 12/2002 | Sheppard et al. | |
| 6,500,157 B2 | 12/2002 | Luther | |
| 6,520,938 B1 | 2/2003 | Funderburk et al. | |
| 6,558,353 B2 | 5/2003 | Zohmann | |
| 6,585,704 B2 | 7/2003 | Luther et al. | |
| 6,595,954 B1 | 7/2003 | Luther et al. | |
| 6,595,955 B2 | 7/2003 | Ferguson et al. | |
| 6,616,630 B1 | 9/2003 | Woehr et al. | |
| 6,623,458 B2 | 9/2003 | Woehr et al. | |
| 6,629,959 B2 | 10/2003 | Kuracina et al. | |
| 6,641,564 B1 | 11/2003 | Kraus | |
| 6,652,486 B2 | 11/2003 | Bialecki et al. | |
| 6,652,490 B2 | 11/2003 | Howell | |
| 6,663,592 B2 | 12/2003 | Rhad et al. | |
| 6,689,102 B2 | 2/2004 | Greene | |
| 6,692,471 B2 | 2/2004 | Boudreaux | |
| 6,695,814 B2 | 2/2004 | Greene et al. | |
| 6,709,419 B2 | 3/2004 | Woehr | |
| 6,709,428 B2 | 3/2004 | Sagstetter | |
| 6,749,588 B1 | 6/2004 | Howell et al. | |
| 6,761,706 B2 | 7/2004 | Vaillancourt | |
| 6,786,875 B2 | 9/2004 | Barker et al. | |
| 6,796,962 B2 | 9/2004 | Ferguson et al. | |
| 6,811,545 B2 | 11/2004 | Vaillancourt | |
| 6,837,878 B2 | 1/2005 | Smutney et al. | |
| 6,860,871 B2 | 3/2005 | Kuracina et al. | |
| 6,863,659 B2 | 3/2005 | Sharpe | |
| 6,902,546 B2 | 6/2005 | Ferguson | |
| 6,916,311 B2 | 7/2005 | Vojtasek | |
| 6,923,793 B2 | 8/2005 | Ishida et al. | |
| 6,972,002 B2 | 12/2005 | Thorne | |
| 6,981,965 B2 | 1/2006 | Luther et al. | |
| 6,984,213 B2 | 1/2006 | Horner et al. | |
| RE38,996 E | 2/2006 | Crawford et al. | |
| 7,004,927 B2 | 2/2006 | Ferguson et al. | |
| 7,008,402 B2 | 3/2006 | Ferguson et al. | |
| 7,018,344 B2 | 3/2006 | Bressler et al. | |
| 7,024,749 B2 | 4/2006 | Sagstetter | |
| 7,083,600 B2 | 8/2006 | Meloul | |
| 7,112,191 B2 | 9/2006 | Daga | |
| 7,125,397 B2 | 10/2006 | Woehr et al. | |
| 7,150,725 B2 | 12/2006 | Wilkinson | |
| 7,153,276 B2 | 12/2006 | Barker et al. | |
| 7,160,269 B2 | 1/2007 | Woehr | |
| 7,179,244 B2 | 2/2007 | Smith et al. | |
| 7,186,239 B2 | 3/2007 | Woehr | |

| | | |
|---|---|---|
| 7,207,975 B2 | 4/2007 | Miller |
| 7,214,208 B2 | 5/2007 | Vaillancourt et al. |
| 7,214,211 B2 | 5/2007 | Woehr et al. |
| 7,226,434 B2 | 6/2007 | Carlyon et al. |
| 7,238,169 B2 | 7/2007 | Takagi et al. |
| 7,247,148 B2 | 7/2007 | Murashita |
| 7,255,685 B2 | 8/2007 | Pressly, Sr. et al. |
| 7,264,613 B2 | 9/2007 | Woehr et al. |
| 2001/0014786 A1 | 8/2001 | Greene et al. |
| 2001/0018573 A1 | 8/2001 | Woehr |
| 2001/0027298 A1 | 10/2001 | Vojtasek |
| 2001/0029356 A1 | 10/2001 | Vojtasek |
| 2001/0053895 A1 | 12/2001 | Vaillancourt |
| 2002/0004650 A1 | 1/2002 | Kuracina et al. |
| 2002/0045843 A1 | 4/2002 | Barker et al. |
| 2002/0099335 A1 | 7/2002 | Zohmann |
| 2002/0103463 A1 | 8/2002 | Luther et al. |
| 2002/0151850 A1 | 10/2002 | Ferguson et al. |
| 2002/0165497 A1 | 11/2002 | Greene |
| 2002/0169418 A1 | 11/2002 | Menzi et al. |
| 2002/0177818 A1 | 11/2002 | Vaillancourt |
| 2002/0193745 A1 | 12/2002 | Ferguson |
| 2003/0004471 A1 | 1/2003 | Hung et al. |
| 2003/0018301 A1 | 1/2003 | Sheppard et al. |
| 2003/0040710 A1 | 2/2003 | Polidoro |
| 2003/0060771 A1 | 3/2003 | Bialecki et al. |
| 2003/0060774 A1 | 3/2003 | Woehr et al. |
| 2003/0100868 A1 | 5/2003 | Ferguson et al. |
| 2003/0105431 A1 | 6/2003 | Howell |
| 2003/0109833 A1 | 6/2003 | Sharpe |
| 2003/0114797 A1 | 6/2003 | Vaillancourt et al. |
| 2003/0120222 A1 | 6/2003 | Vaillancourt |
| 2003/0144627 A1 | 7/2003 | Woehr et al. |
| 2003/0171718 A1 | 9/2003 | DeLegge et al. |
| 2003/0195471 A1 | 10/2003 | Woehr et al. |
| 2003/0195475 A1 | 10/2003 | Ferguson et al. |
| 2003/0195479 A1 | 10/2003 | Kuracina et al. |
| 2003/0216687 A1 | 11/2003 | Hwang |
| 2003/0220617 A1 | 11/2003 | Dickerson |
| 2004/0010227 A1 | 1/2004 | Riesenberger et al. |
| 2004/0030289 A1 | 2/2004 | Vitullo et al. |
| 2004/0049155 A1 | 3/2004 | Schramm |
| 2004/0049163 A1 | 3/2004 | Murashita |
| 2004/0078002 A1 | 4/2004 | Rhad et al. |
| 2004/0078003 A1 | 4/2004 | Smith et al. |
| 2004/0092879 A1 | 5/2004 | Kraus et al. |
| 2004/0092885 A1 | 5/2004 | Duchon et al. |
| 2004/0092889 A1 | 5/2004 | Ferguson et al. |
| 2004/0102740 A1 | 5/2004 | Meloul |
| 2004/0116856 A1 | 6/2004 | Woehr et al. |
| 2004/0116864 A1 | 6/2004 | Boudreaux |
| 2004/0122380 A1 | 6/2004 | Utterberg |
| 2004/0133167 A1 | 7/2004 | Ferguson et al. |
| 2004/0138628 A1 | 7/2004 | Woehr |
| 2004/0162522 A1 | 8/2004 | Woehr |
| 2004/0162525 A1 | 8/2004 | Vaillancourt et al. |
| 2004/0162526 A1 | 8/2004 | Vaillancourt et al. |
| 2004/0171989 A1 | 9/2004 | Horner et al. |
| 2004/0186434 A1 | 9/2004 | Harding et al. |
| 2004/0204681 A1 | 10/2004 | Thoresen et al. |
| 2004/0225260 A1 | 11/2004 | Villa et al. |
| 2004/0236289 A1 | 11/2004 | Ferguson et al. |
| 2004/0243061 A1 | 12/2004 | McGurk |
| 2005/0004521 A1 | 1/2005 | Zohmann |
| 2005/0004532 A1 | 1/2005 | Woehr et al. |
| 2005/0027256 A1 | 2/2005 | Barker et al. |
| 2005/0027263 A1 | 2/2005 | Woehr et al. |
| 2005/0043691 A1 | 2/2005 | Ferguson |
| 2005/0049559 A1 | 3/2005 | Mathias |
| 2005/0059937 A1* | 3/2005 | Ferguson ............ 604/263 |
| 2005/0070855 A1 | 3/2005 | Ferguson et al. |
| 2005/0075609 A1 | 4/2005 | Latona |
| 2005/0096592 A1 | 5/2005 | Carlyon et al. |
| 2005/0113755 A1 | 5/2005 | Greene et al. |
| 2005/0113758 A1 | 5/2005 | Smutney et al. |
| 2005/0182362 A1 | 8/2005 | Sircom et al. |
| 2005/0182363 A1 | 8/2005 | Kulli |
| 2005/0182369 A1 | 8/2005 | Miller |
| 2005/0192535 A1 | 9/2005 | Takagi et al. |
| 2005/0192536 A1 | 9/2005 | Takagi et al. |
| 2005/0273057 A1 | 12/2005 | Popov |
| 2005/0277879 A1 | 12/2005 | Daga |
| 2006/0041231 A1 | 2/2006 | Pressly, Sr. et al. |
| 2006/0058742 A1 | 3/2006 | Cha et al. |
| 2006/0074384 A1 | 4/2006 | Kohler |
| 2006/0079844 A1 | 4/2006 | Whisson et al. |
| 2006/0116638 A1 | 6/2006 | Woehr et al. |
| 2006/0129101 A1 | 6/2006 | McGuckin, Jr. |
| 2006/0155244 A1 | 7/2006 | Popov |
| 2006/0155245 A1 | 7/2006 | Woehr |
| 2006/0155246 A1 | 7/2006 | Higuchi et al. |
| 2006/0161116 A1 | 7/2006 | Willis et al. |
| 2006/0178635 A1 | 8/2006 | Callaway |
| 2006/0184116 A1 | 8/2006 | Takagi et al. |
| 2006/0184125 A1 | 8/2006 | Woehr |
| 2006/0189934 A1 | 8/2006 | Kuracina et al. |
| 2006/0264828 A1 | 11/2006 | Woehr et al. |
| 2006/0270980 A1 | 11/2006 | Menzi et al. |
| 2007/0038179 A1 | 2/2007 | Bialecki et al. |
| 2007/0038181 A1 | 2/2007 | Melamud et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0038186 A1 | 2/2007 | Sutton et al. |
| 2007/0038187 A1 | 2/2007 | Albert et al. |
| 2007/0038188 A1* | 2/2007 | Bialecki et al. ........ 604/164.08 |
| 2007/0049868 A1 | 3/2007 | Woehr et al. |
| 2007/0055203 A1 | 3/2007 | Miller |
| 2007/0060889 A1 | 3/2007 | Adams |
| 2007/0073221 A1 | 3/2007 | Bialecki et al. |
| 2007/0073222 A1 | 3/2007 | Lilley, Jr. et al. |
| 2007/0083159 A1 | 4/2007 | Woehr et al. |
| 2007/0083167 A1 | 4/2007 | Smith et al. |
| 2007/0100297 A1 | 5/2007 | Woehr et al. |
| 2007/0106231 A1 | 5/2007 | Snow et al. |
| 2007/0112305 A1 | 5/2007 | Brimhall |
| 2007/0129689 A1 | 6/2007 | Woehr et al. |
| 2007/0149928 A1 | 6/2007 | Kulli |
| 2007/0156093 A1 | 7/2007 | Woehr |
| 2007/0161950 A1 | 7/2007 | Carlyon et al. |
| 2007/0179446 A1 | 8/2007 | Carrez et al. |
| 2007/0179447 A1 | 8/2007 | Carrez et al. |
| 2007/0191771 A1 | 8/2007 | Moyer |
| 2007/0191775 A1 | 8/2007 | Diep et al. |
| 2007/0191776 A1 | 8/2007 | Bialecki et al. |
| 2007/0191777 A1 | 8/2007 | King |
| 2007/0191782 A1 | 8/2007 | Wilkinson |
| 2007/0232995 A1 | 10/2007 | Samsoondar |
| 2007/0250057 A1 | 10/2007 | Nobis et al. |

FOREIGN PATENT DOCUMENTS

| | | |
|---|---|---|
| EP | 1752182 A2 | 2/2007 |
| JP | 7148176 A | 6/1995 |
| JP | 2003506160 A | 2/2003 |
| JP | 2007509723 A | 4/2007 |
| WO | 9959660 A1 | 11/1999 |
| WO | 0110488 A1 | 2/2001 |

OTHER PUBLICATIONS

U.S. Appl. No. 12/313,661 filed Nov. 21, 2008, Meehan et al.
U.S. Appl. No. 12/275,636, filed Nov. 21, 2008, Delano.

* cited by examiner

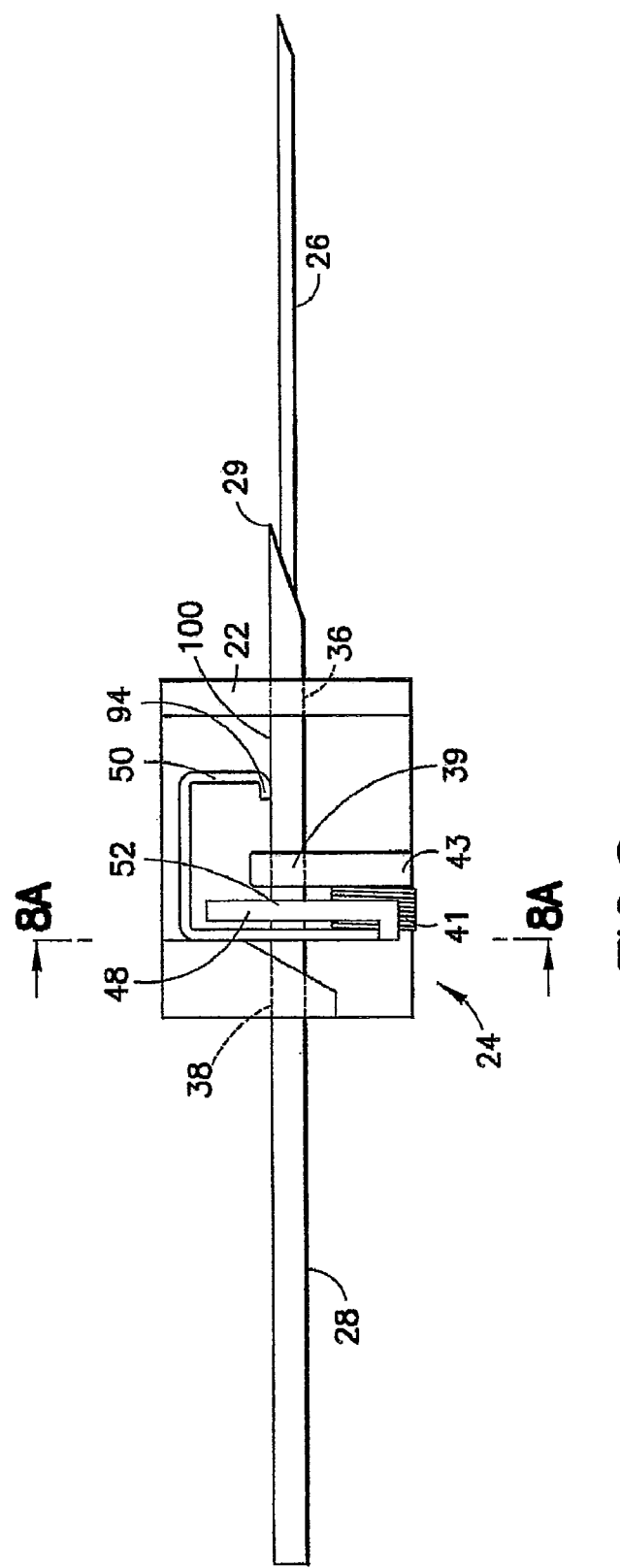

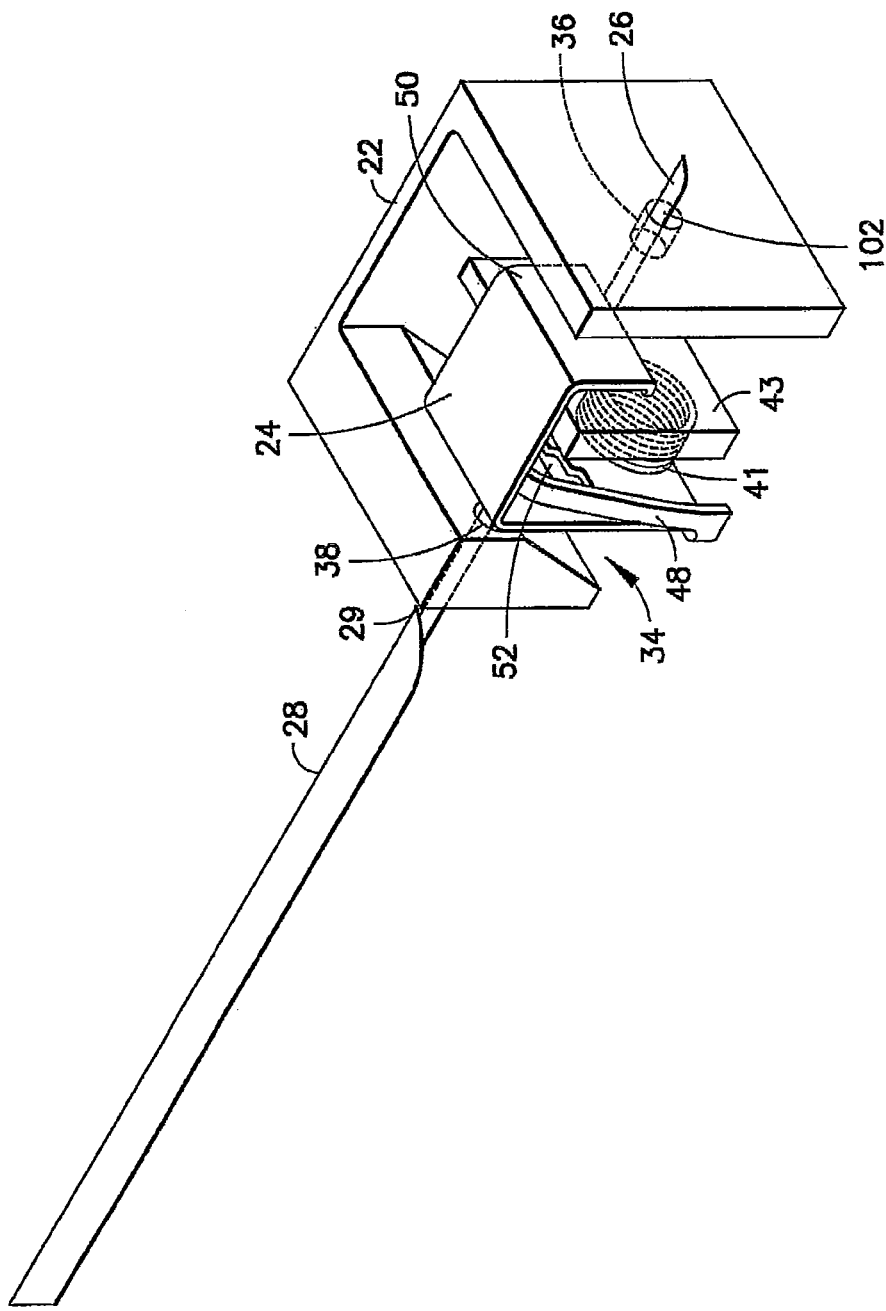

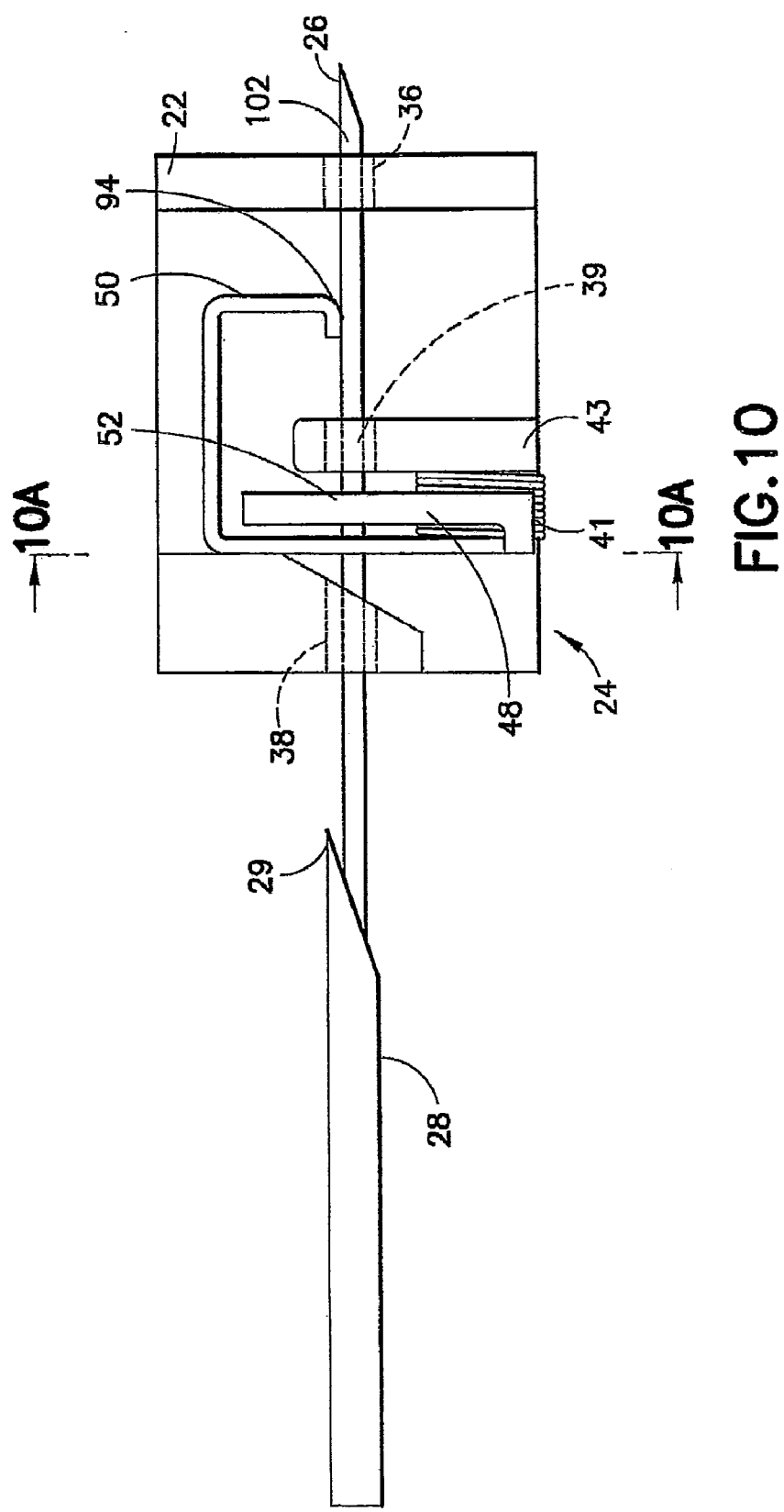

SAFETY NEEDLE GUARD

CROSS REFERENCE TO RELATED APPLICATION

This application claims priority to U.S. Provisional Patent Application No. 60/989,544, filed Nov. 21, 2007, entitled "Safety Needle Guard", the entire disclosure of which is herein incorporated by reference.

BACKGROUND OF THE INVENTION

1. Field of the Invention

The subject invention relates generally to medical needles and, more particularly, to medical needles having a safety device for shielding the needle tip after withdrawal of the needle from a patient.

2. Description of Related Art

In order to adequately protect medical practitioners from inadvertent puncture and/or wounding from medical sharps, such as needles and syringes, safety shielding devices have been developed to limit the exposure from contaminated medical devices. In many procedures, the greatest avoidable risk of accidental needle puncture, also referred to as a "needlestick", occurs during handling of the used needle, such as when a medical practitioner inserts the used needle into a protective sheath for disposal. This action usually requires the practitioner to move the hand which holds the sheath toward the needle tip. Any inaccuracy in this movement increases the probability of an accidental needlestick. This is particularly true for "long needles" commonly used in spinal and epidural procedures, in which the handle portion of the device is separated from the needle tip by a substantial distance.

Prior safety devices have been developed, which include a protective guard specifically dimensioned to surround and bind a predetermined needle size. The prior safety devices have been initially stored on the needle at a location remote from the patient tip. After use, the safety device is typically advanced over the patient tip to shield the medical practitioner. In view of the fact that prior safety devices have been dimensioned to accommodate a single gauge needle, a multitude of safety devices, corresponding to all utilized needle gauges, have been necessary. This contributes to increased manufacturing costs and stocking concerns.

In addition, in medical procedures utilizing long needles, it is common practice to first insert an introducer sheath into the patient, and subsequently introduce an inner cannula therethrough. Typically, both the inner cannula and the introducer sheath include a sharp pointed profile. Since the prior safety devices have been specifically designed to accommodate a single needle gauge, medical procedures utilizing an introducer sheath and an inner cannula have typically been performed without a safety device.

SUMMARY OF THE INVENTION

The present invention is directed to a single needle guard that is capable of shielding a plurality of needle gauges. In addition, the needle guard of the present invention is capable of transitioning from a first cannula dimension, such as corresponding to the dimension of an introducer sheath, to a second cannula dimension, such as corresponding to the dimension of an inner cannula.

In one embodiment, a needle guard includes a binding plate defining a multi-slot aperture adapted to receive a needle cannula therethrough. The needle guard also includes a biasing member biasing the needle cannula within the multi-slot aperture, and a sensing arm connected to the binding plate, adapted to contact a portion of the needle cannula, and positionable for restricting movement of the needle cannula.

The biasing member may be disposed adjacent the multi-slot aperture. The multi-slot aperture may include a first region having a first dimension, and a second region having a second dimension, with the second dimension being smaller than the first dimension. The biasing member may be initially positioned adjacent the first region of the multi-slot aperture. The biasing member may also be adapted to apply a biasing force adjacent the multi-slot aperture in a direction that is substantially perpendicular to a through-axis of the multi-slot aperture. The biasing member may be adapted to advance the needle cannula within the multi-slot aperture from the first region to the second region in a direction perpendicular to a longitudinal axis of the needle cannula. The sensing arm may further include a transverse barrier. The transverse barrier may include a base plate connected to the binding plate and extending in a distal direction from the binding plate. The transverse barrier may also include an engagement plate connected to, and extending from, the base plate in a direction toward a through-axis of the multi-slot aperture. The engagement plate may include a contact surface for contacting a portion of the needle cannula at a location distal from the multi-slot aperture. The contact surface may include an angled restraining lip extending toward the multi-slot aperture. The needle guard may also include a biasing element biasing the binding plate in a distal to proximal direction to bias the binding plate toward a tilted position. The needle guard may further include a second biasing element biasing the binding plate in a direction substantially aligned with the multi-slot aperture.

In another embodiment, a needle guard includes a housing, defining an interior, and having a first port and a second port extending therethrough and aligned along an axis of the housing. The needle guard also includes a locking mechanism disposed within the interior of the housing. The locking mechanism includes a binding plate defining a multi-slot aperture, with at least a portion of the multi-slot aperture aligned with the first port and the second port along the axis of the housing. The first port, the second port, and the multi-slot aperture are adapted to receive a needle cannula therethrough. The needle guard also includes a biasing member for biasing the needle cannula within the aperture. The needle guard also includes a sensing arm connected to the binding plate adapted to contact the needle cannula, and positionable for restricting movement of the needle cannula.

The biasing member may be disposed adjacent the multi-slot aperture. The interior of the housing may include an angled interior surface for accommodating a portion of the binding plate thereagainst. The multi-slot aperture may include a first region having a first dimension, and a second region having a second dimension, the second dimension being smaller than the first dimension. The biasing member may be adapted to apply a biasing force adjacent the multi-slot aperture in a direction that is substantially perpendicular to a through-axis of the multi-slot aperture.

The sensing arm may include a transverse barrier. The transverse barrier may include a base plate connected to the binding plate and extending in a distal direction from the binding plate. The transverse barrier may also include an engagement plate connected to, and extending from, the base plate in a direction toward a through-axis of the multi-slot aperture. The engagement plate may include a contact surface for contacting a portion of the needle cannula at a location distal from the multi-slot aperture. The contact surface may include an angled restraining lip extending toward the multi-slot aperture. The locking mechanism may be adapted to pivot within the interior of the housing about a pivoting axis to position the sensing arm to restrict movement of the needle cannula. The needle guard may also include a biasing element biasing the binding plate in a distal to proximal direction to bias the binding plate toward a tilted position. The needle guard may further include a second biasing element biasing the binding plate in a direction substantially aligned with the multi-slot aperture.

In another embodiment, a device includes a needle cannula having a cannula tip, and a housing disposed about a portion of the needle cannula. The housing defines an interior, and includes a first port and a second port extending therethrough and aligned along an axis of the housing. The device also includes a locking mechanism disposed within the interior of the housing. The locking mechanism includes a binding plate defining a multi-slot aperture, at least a portion of the multi-slot aperture aligned with the first port and the second port along the axis of the housing. The first port, the second port, and the multi-slot aperture are adapted to receive the needle cannula therethrough. The device also includes a biasing member for biasing the needle cannula within the aperture, the biasing member positionable for restricting movement of the needle cannula in at least a first direction. The device further includes a transverse barrier connected to the binding plate adapted to contact a portion of the needle cannula, and positionable for restricting movement of the needle cannula in a second direction, the second direction being substantially different from the first direction, such as in an opposite direction.

The biasing member may be disposed adjacent the multi-slot aperture. The transverse barrier may include a base plate connected to the binding plate and extending in a distal direction from the binding plate. The transverse barrier may also include an engagement plate connected to, and extending from, the base plate in a direction toward a through-axis of the multi-slot aperture. The engagement plate may include a contact surface for contacting a portion of the needle cannula at a location distal from the multi-slot aperture.

The contact surface may include an angled restraining lip extending toward the multi-slot aperture in a direction that is substantially parallel to the through-axis of the multi-slot aperture. The transverse barrier may include a contact surface, and the transverse barrier is restrained from restricting movement of the needle cannula by contact between the contact surface and the needle cannula. The transverse barrier may be positioned to restrict movement of the needle cannula in the distal direction when contact between the contact surface and the needle cannula is interrupted.

The locking mechanism may be adapted to pivot within the interior of the housing about a pivoting axis to position the sensing arm to restrict movement of the needle cannula. The locking mechanism may be adapted to pivot about the pivoting axis when contact between a contact surface of the sensing arm and the needle cannula is interrupted. The interior of the housing may include an angled interior surface for accommodating a portion of the binding plate thereagainst. The multi-slot aperture may also include a first region having a first dimension, and a second region having a second dimension, the second dimension being smaller than the first dimension.

The biasing member may be adapted to bias the needle cannula against the first port and the second port of the housing in a restrained position, and against at least a portion of the multi-slot aperture in an activated position. The biasing member may also be adapted to advance the needle cannula within the multi-slot aperture from the first region to the second region. The device may also include a biasing element biasing the binding plate in a distal to proximal direction to bias the binding plate toward a tilted position. The needle guard may further include a second biasing element biasing the binding plate in a direction substantially aligned with the multi-slot aperture.

In another embodiment, a method of actuating a needle guard includes the step of providing a needle guard disposed about at least a portion of a needle cannula. The needle guard includes a housing, defining an interior, and having a first port and a second port extending therethrough and aligned along an axis of the housing. The needle guard also includes a locking mechanism disposed within the interior of the housing. The locking mechanism includes a binding plate defining a multi-slot aperture, at least a portion of the multi-slot aperture aligned with the first port and the second port along the axis of the housing. The first port, the second port, and the multi-slot aperture are adapted to receive the needle cannula therethrough. The needle guard further includes a biasing member for biasing the needle cannula within the aperture. The needle guard also includes a sensing arm connected to the binding plate and comprising a contact surface. The sensing arm is adapted to transition from a restrained position in which the contact surface contacts a portion of the needle cannula, to an activated position in which the sensing restricts movement of the needle cannula. The needle guard also includes at least one biasing element for biasing the binding plate in a distal to proximal direction. The method also includes the step of transitioning the sensing arm from the restrained position to the activated position by interrupting contact between the contact surface and the needle cannula.

BRIEF DESCRIPTION OF THE DRAWINGS

FIG. 8 is a side view of the device of FIG. 6 in the restrained position.

FIG. 9 is a perspective view of the device of FIG. 7 in the intermediate restrained position having the outer cannula withdrawn from the first port and the second port of the housing and the inner cannula extending through the first port and the second port of the housing in accordance with an embodiment of the present invention.

FIG. 10 is a side view of the device of FIG. 9 in the intermediate restrained position.

DESCRIPTION OF THE PREFERRED EMBODIMENTS

Figure 1:
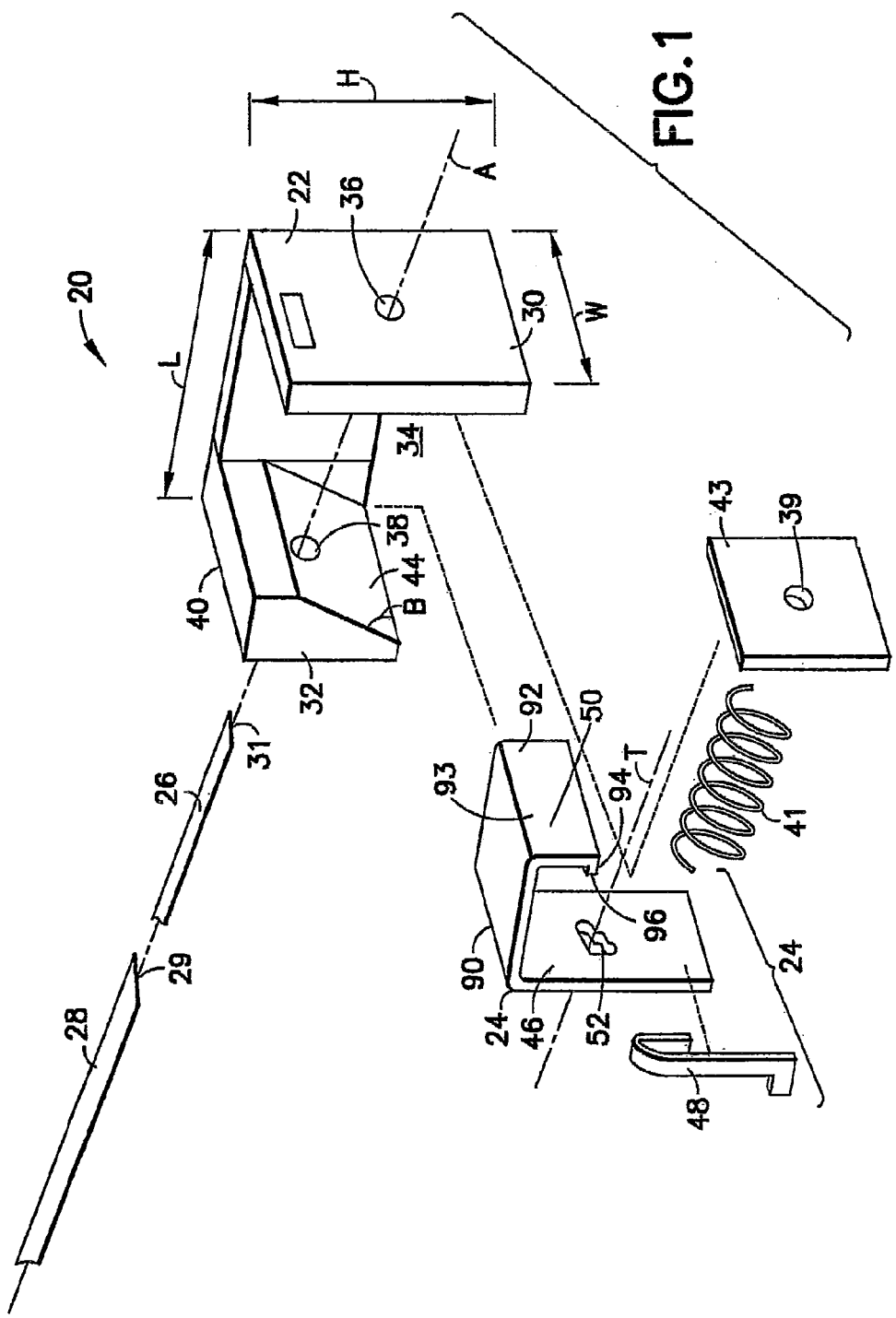
FIG. 1 is an exploded perspective view of a device including an outer needle cannula, an inner needle cannula, a needle guard, and a needle guard housing in accordance with an embodiment of the present invention.

For purposes of the description hereinafter, the words "upper", "lower", "right", "left", "vertical", "horizontal", "top", "bottom", "lateral", "longitudinal" and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Referring to FIG. 1, the device 20 of the present invention includes a housing 22, a locking mechanism, such as a needle guard 24 disposed within the housing 22, and a outer needle cannula 28 also disposed within the housing 22 and extending through a portion of the needle guard 24. The housing 22 includes a first end 30 and a second end 32 opposite the first end 30, and defines an interior cavity 34 therebetween. The first end 30 defines a first port 36, and the second end 32 defines a second port 38 substantially aligned with the first port 36 along a longitudinal axis A of the housing 22. The first port 36 and the second port 38 may be substantially the same size and may have substantially the same diameter. In another embodiment, one of the first port 36 and the second port 38 may be larger than the other of the first port 36 and the second port 38.

In one embodiment, the housing 22 of the present invention is adapted to accommodate a portion of an outer needle cannula 28, having a needle tip 29, through the first port 36 and the second port 38. In one embodiment, the first port 36 and the second port 38 may have a diameter that is slightly greater than the diameter of the outer needle cannula 28. In another embodiment, the first port 36 and the second port 38 may have a diameter that is considerably larger than the diameter of the outer needle cannula 28. The housing 22 of the present invention may accommodate a needle cannula having, for example, a diameter of from about 18 G to about 27 G, through the first port 36 and the second port 38. In another embodiment, the housing 22 of the present invention may accommodate multiple nested needle cannulae through the first port 36 and the second port 38, such as an outer needle cannula 28 having a needle tip 29, and an inner needle cannula 26 having a needle tip 31, nested within the outer needle cannula 28. In one embodiment, the outer needle cannula 28 may be an introducer sheath and the inner needle cannula 26 may be a smaller diameter needle for delivering fluid to a patient or extracting a fluid from a patient. Alternatively, the inner needle cannula 26 may include a solid stylet for providing rigidity to an outer needle cannula 28. In a further embodiment, the housing 22 may be adapted for use with conventional gauge "long" needle(s) suitable for spinal, epidural, or anesthesia procedures, and the like. In yet a further embodiment, the housing 22 may be adapted for use with 18 G-29 G needle cannula.

The housing 22 may have any suitable dimensions and exterior configurations, provided the first port 36, second port 38, and at least a portion of the interior cavity 34 are sufficiently sized to accommodate the outer needle cannula 28, and/or nested inner needle cannula 26 and outer needle cannula 28 therethrough. In one embodiment, the housing 22 may have a length L, as shown in FIG. 1, of from about 0.25 inch to about 1.50 inches, a width W, shown in FIG. 1, of from about 0.125 inch to about 1 inch, and a height H, also shown in FIG. 1, of from about 0.25 inch to about 1.50 inches. Although the housing 22 of the present invention is shown substantially as a substantially rectangular shape with three open sides, it is anticipated herein that the housing 22 may be fully enclosed, i.e., fully surrounding the interior cavity 34, and/or fully enclosed within a separate exterior housing (not shown). It is also contemplated herein that the exterior surface 40 of the housing 22 may have any suitable shape, such as rectangular, square, ovoid, trapezoid, and the like. The housing 22 may be made of any suitable material, such as a substantially rigid polymeric composition. Optionally, the housing 22 may also include a gripable region having a textured surface and/or texture enhancing coating applied thereto for facilitating a medical practitioner to easily grab the housing 22.

The housing 22 may also include at least one angled interior surface 44, such as disposed within the second end 32 adjacent the second port 38. The angled interior surface 44 may have an angle B of from about 30° to about 60°. The housing 22 also includes a resistance plate 43 disposed within the interior cavity 34 of the housing, such as between the first end 30 and the second end 32. The resistance plate 43 includes a third port 39 which is aligned with the first port 36 and the second port 38 to allow a cannula to pass therethrough.

The present invention also includes a needle guard 24 having a binding plate 46, a biasing member 48 and a sensing arm 50 disposed within the interior cavity 34 of the housing 22. As shown in FIGS. 1-3B, the binding plate 46 defines a multi-slot aperture 52 extending therethough. As used herein, the term "multi-slot aperture" means an aperture having a first region having a first dimension, and a second region contiguous with the first region and having a second dimension, as measured in the same orientation as the first dimension, the second dimension being smaller than the first dimension.

Figure 3:
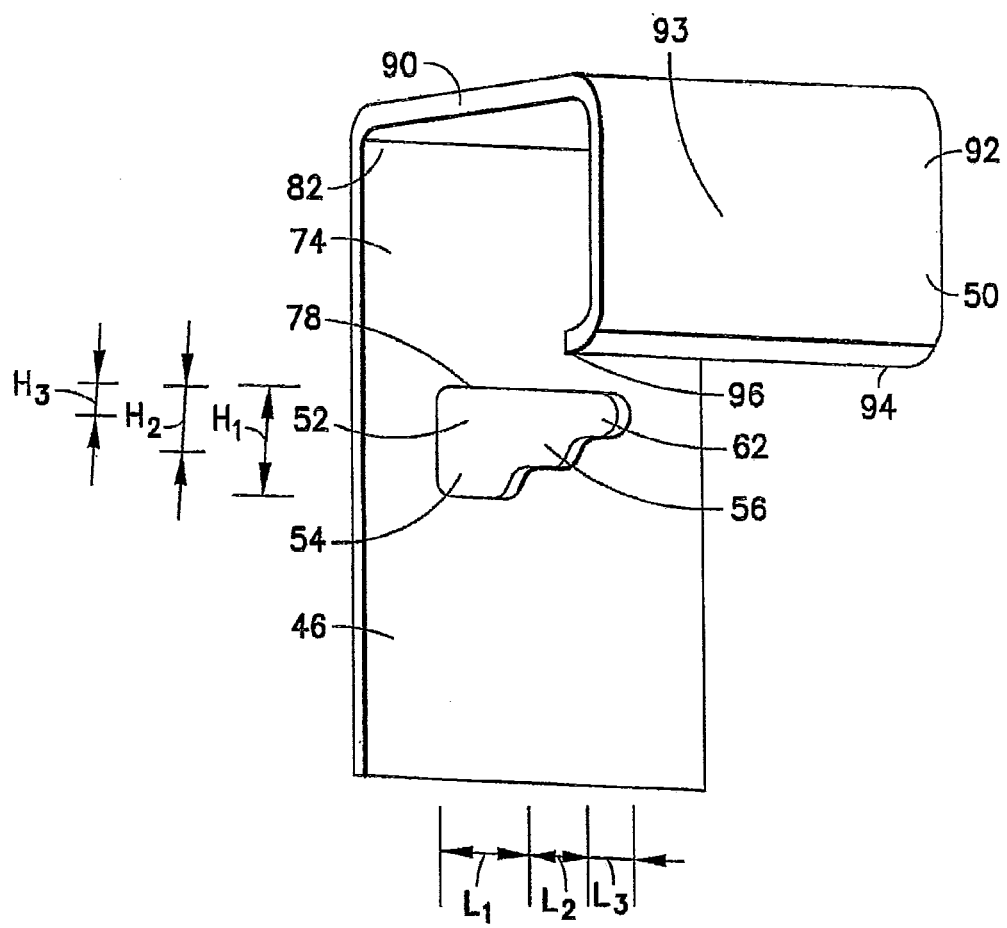
FIG. 3 is a perspective view of an embodiment of a binding plate having a multi-slot aperture and sensing arm in accordance with an embodiment of the present invention.
Figure 3A:
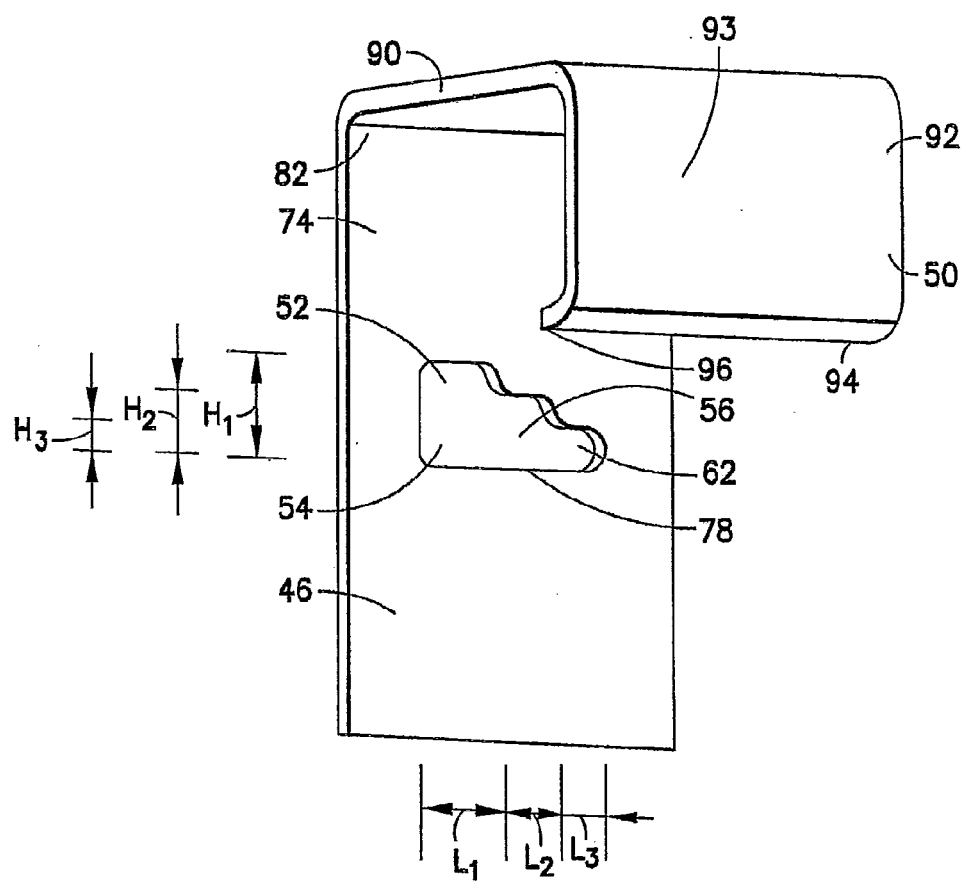
FIG. 3A is a perspective view of an embodiment of a binding plate having an inverted multi-slot aperture and sensing arm in accordance with an embodiment of the present invention.
Figure 3B:
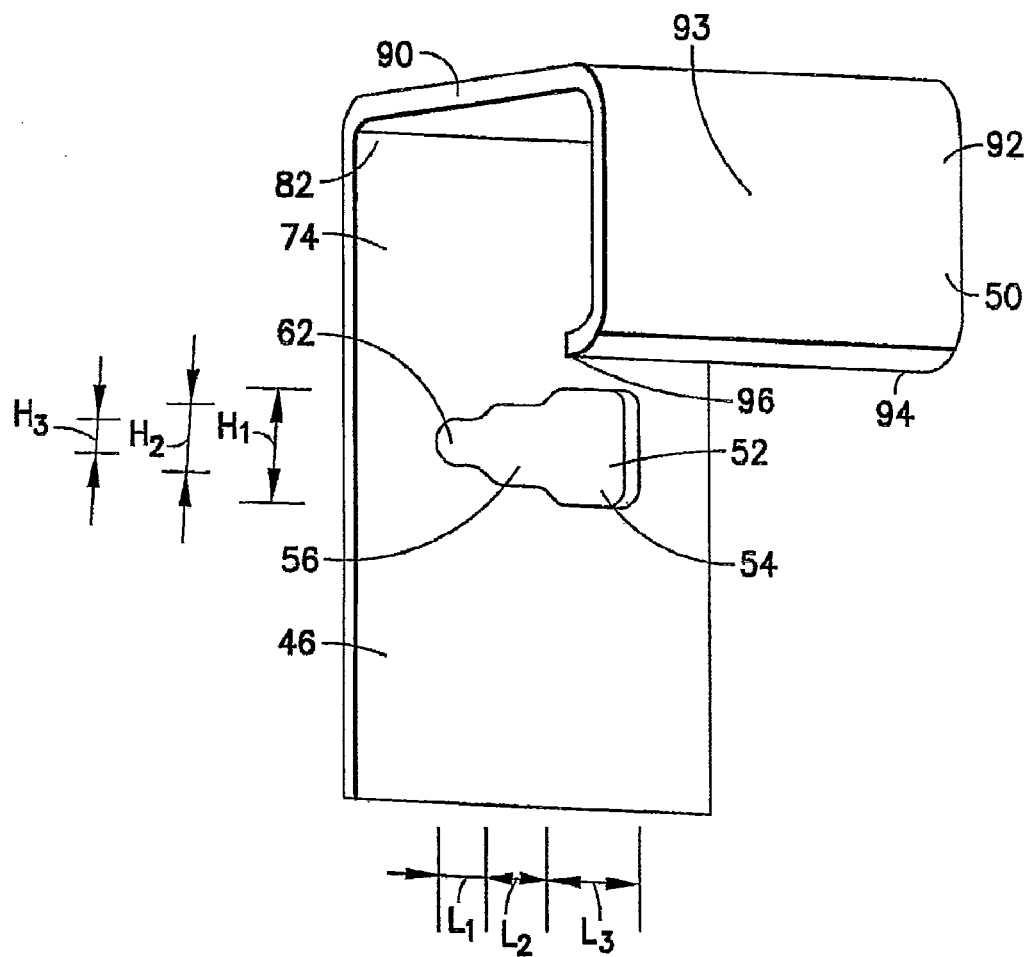
FIG. 3B is a perspective view of an embodiment of a binding plate having a stepped multi-slot aperture and sensing arm in accordance with an embodiment of the present invention.

For example, as shown in FIGS. 3-3B, the multi-slot aperture 52 may have a first region 54 having a first dimension $H_1$, and a second region 56 having a second dimension $H_2$, the second dimension $H_2$ being smaller than the first dimension $H_1$. In addition, the multi-slot aperture 52 may have a third region 62 having a third dimension $H_3$, the third dimension $H_3$ being smaller than the second dimension $H_2$. Optionally, the first dimension $H_1$, the second dimension $H_2$, and the third dimension $H_3$, each represent the respective heights of the first region 54, the second region 56 and the third region 62. Similarly, the multi-slot aperture 52 may have a first region 54 having a first opposing dimension $L_1$, and a second region 56 having a second opposing dimension $L_2$, the second opposing dimension $L_2$ being smaller than the first opposing dimension $L_1$, and likewise may have a third region 62 having a third opposing dimension $L_3$, the third opposing dimension $L_3$ being smaller than the second opposing dimension $L_2$. Optionally, the first opposing dimension $L_1$, the second opposing dimension $L_2$, and the third opposing dimension $L_3$, each represent the respective lengths of the first region 54, the second region 56 and the third region 62. Alternatively, the multi-slot aperture 52 may include a first region 54 having a first dimension $H_1$ and a first opposing dimension $L_1$, and a second region 56 having a second dimension $H_2$ and a second opposing dimension $L_2$, with the second dimension $H_2$ being smaller than the first dimension $H_1$ and the first opposing dimension $L_1$ and the second opposing dimension $L_2$ being equal.

In yet another embodiment, the first opposing dimension $L_1$, may be equal to or greater than the first dimension $H_1$, the second opposing dimension $L_2$, may be equal to or greater than the second dimension $H_2$, and the third opposing dimension $L_3$, may be equal to or greater than the third dimension $H_3$. It is also anticipated herein, that the multi-slot aperture 52 may include additional regions, such as a fourth or fifth region (not shown), each respectively having a dimension successively smaller than the previous region. In yet another embodiment, the first dimension $H_1$ and the second dimension $H_2$ may be selected to be slightly larger than the outer diameter of a target cannula gauge intended to be received therein. For example, the first dimension $H_1$ may be dimensioned to receive an outer cannula therein, whereas the second dimension $H_2$ may be dimensioned to receive an inner cannula therein and to prevent receipt of an outer cannula therein. In yet another example, the first dimension $H_1$ of the first region 54 may be dimensioned to allow receipt of an 18 G cannula therein, and the second dimension $H_2$ of the second region 56 may be dimensioned to allow receipt of a 22 G cannula therein but not an 18 G cannula.

Figure 4:
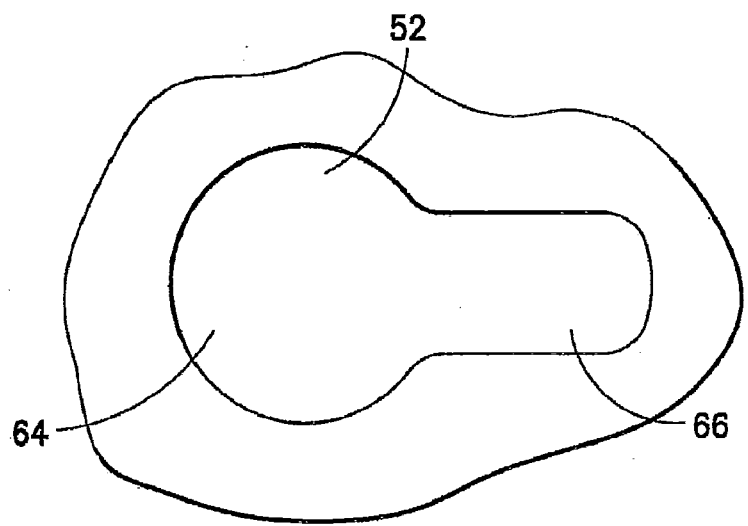
FIG. 4 is a front view of an alternative embodiment of a multi-slot aperture in accordance with an embodiment of the present invention.
Figure 5:
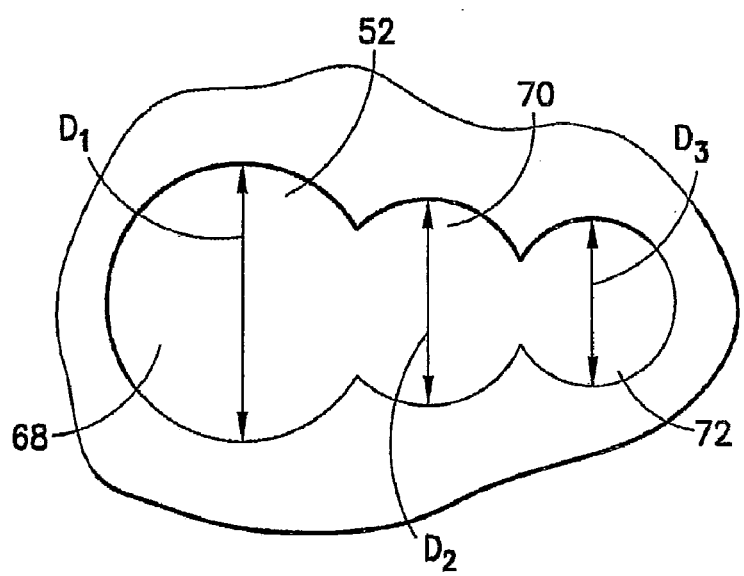
FIG. 5 is a front view of an alternative embodiment of a multi-slot aperture in accordance with an embodiment of the present invention.

As shown in FIG. 4, the multi-slot aperture 52 may include a substantially circular hole portion 64 which is contiguous with a substantially elongated slot portion 66. As shown in FIG. 5, the keyhole region 52 may include a first substantially circular hole region 68 having a first diameter $D_1$, a second substantially circular hole region 70 having a second diameter $D_2$, and a third substantially circular hole region 72 having a third diameter $D_3$. In this configuration, $D_3$ is smaller than $D_2$, and $D_2$ is smaller than $D_1$.

Figure 2:
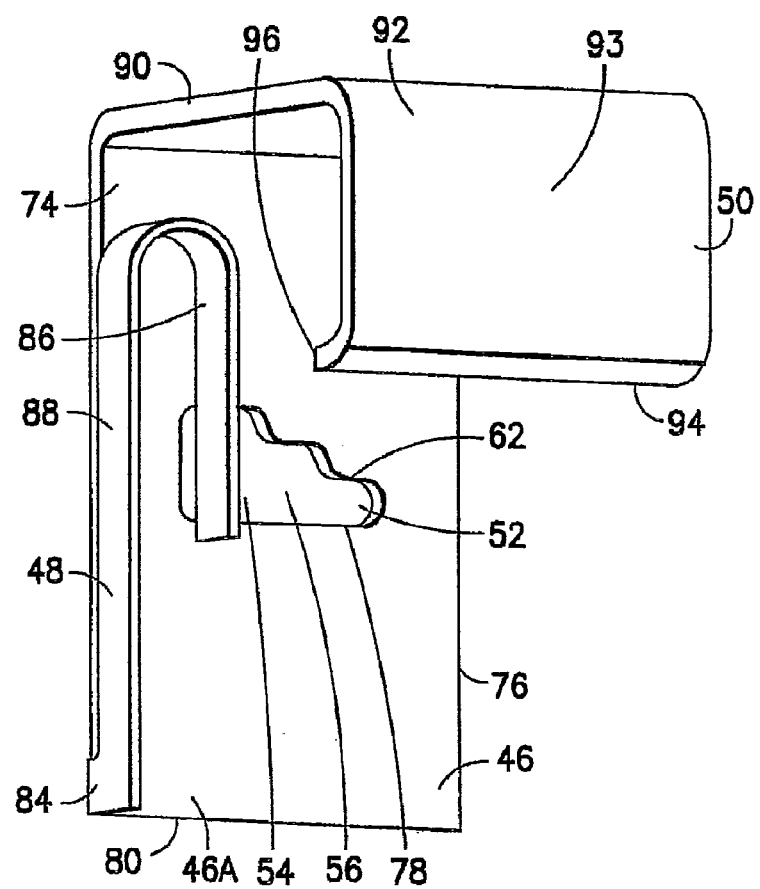
FIG. 2 is a perspective view of the needle guard having a binding plate having an alternative multi-slot aperture, a biasing member, and a sensing arm of FIG. 1 in accordance with an embodiment of the present invention.

Referring to FIG. 2, in one embodiment, the first region 54 is aligned adjacent a biasing member receiving surface 74, such that at least one dimension of the multi-slot aperture 52 transitions from the biasing member receiving surface 74 toward the housing alignment surface 76 in a stepped-down progression. As shown in FIG. 3, the substantially flat surface 78 may be oriented toward the upper surface 82 of the binding plate 46. In another embodiment, as shown in FIG. 3A, in one embodiment the multi-slot aperture 52 may include a substantially flat surface 78 oriented toward the bottom surface 80 of the binding plate 46. In yet another embodiment, shown in FIG. 3B, the first region 54 transitions to the second region 56 in a stepped fashion.

The multi-slot aperture 52 of the present invention is adapted to receive an outer needle cannula 28, as shown in FIG. 1, therethrough. In one embodiment, the first region 54 is adapted to receive an outer needle cannula 28 therethrough and the second region 56 is adapted to prevent the outer needle cannula 28 from being received therein. The second region 56, however, may be adapted to receive the inner needle cannula 26 therein, as will be described.

Referring again to FIGS. 1-2, the needle guard 24 also includes a biasing member 48 initially positioned adjacent the multi-slot aperture 52, such as initially positioned adjacent the first region 54 of the multi-slot aperture 52. The biasing member 48 may include any material and/or structure sufficient to impart a biasing force in a direction substantially perpendicular to a through-axis T of the multi-slot aperture 52, as shown in FIG. 1. In one embodiment, the biasing member 48 is connected to the binding plate 46 at a connection point 84. In another embodiment, the biasing member 48 is restrained against the binding plate 46 by a portion of the housing 22. The biasing member 48 may be a spring, such as a metal arm having a first portion 86 adjacent the multi-slot aperture 52 and a second portion 88 adjacent the biasing member receiving surface 74 of the binding plate 46.

Figure 10A:
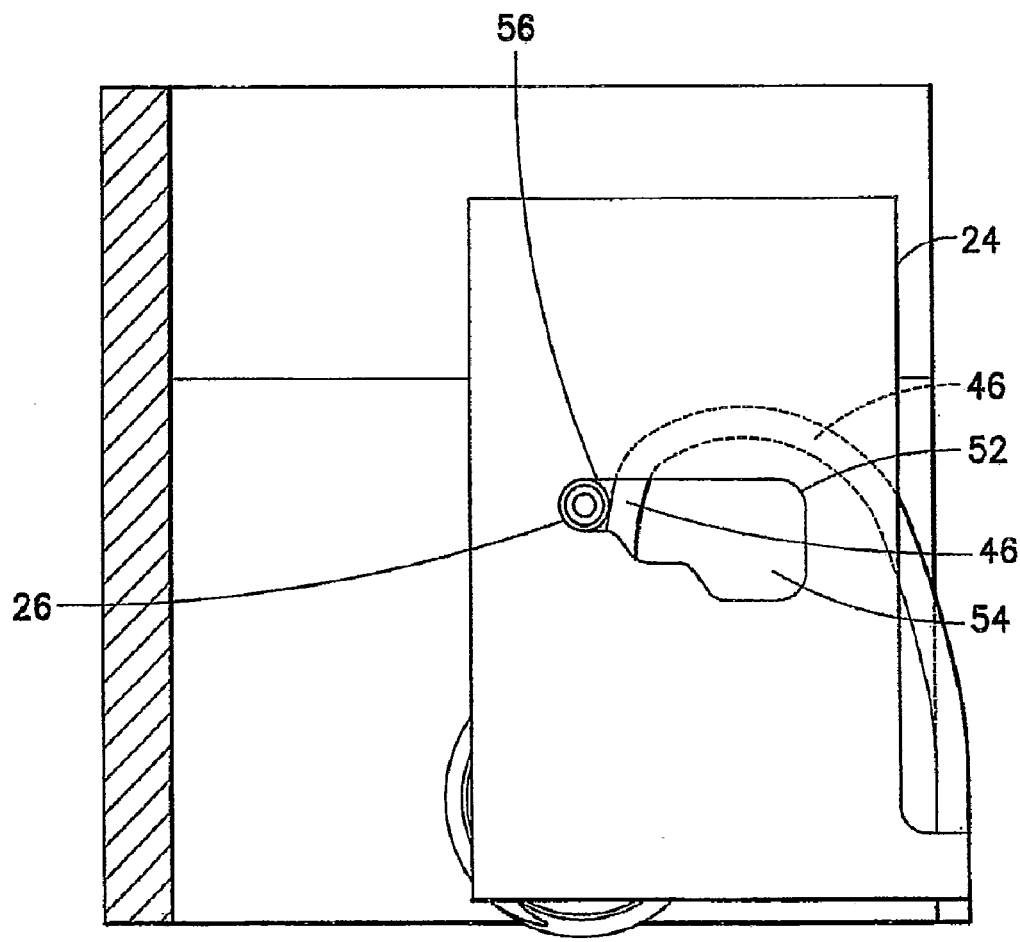
FIG. 10A is a cross-sectional view of the device of FIG. 9 taken along line 10A-10A of FIG. 10.

Referring again to FIGS. 1-3B, the needle guard 24 also includes a sensing arm 50 connected to the binding plate 46, such as adjacent the upper surface 82. In one embodiment, the sensing arm 50 includes a transverse barrier 93 adapted to transition from a restrained position, as shown in FIGS. 7-10, to an activated position, as shown in FIGS. 11-12. In one configuration, the transverse barrier 93 includes a base plate 90 connected to the binding plate 46 and extending in a substantially distal direction from the binding plate 46. The transverse barrier 93 may also include an engagement plate 92 connected to, and extending from, the base plate 90. The engagement plate 92 may extend from the base plate 90 in a direction toward the through-axis T, shown in FIG. 1, of the multi-slot aperture 52. In one embodiment, the engagement plate 92 may be spaced apart from the binding plate 46, a distance of from about 0.125 inch to about 0.5 inch. The binding plate 46 and the sensing arm 50 may be co-formed, or separately assembled and subsequently joined. In a further embodiment, the engagement plate 92 includes a contact surface 94 aligned with the through-axis T of the multi-slot aperture 52. In yet a further embodiment, the contact surface 94 includes an angled restraining lip 96 extending toward the multi-slot aperture 52 in a direction substantially parallel to the through-axis T of the multi-slot aperture 52.

Referring yet again to FIGS. 1-2, a biasing element 41 is also disposed between a portion of the housing 22, such as a portion of the resistance plate 43, and a portion of the needle guard 24, such as a portion of the binding plate 46. The biasing element 41 may also be disposed between a portion of the resistance plate 43 and a portion of the biasing member 48 connected to the binding plate 46. The biasing element 41 biases a lower portion of the needle guard 24, such as lower portion 46A of the binding plate 46, against the housing in a direction parallel to the longitudinal axis A of the housing 22. This biasing force is balanced by the force applied to the needle cannula 28 by the contact from contact surface 94 of the sensing arm 50 and the reaction force of a portion of the housing 22, such as rearward portion 104, at a pivot P, as shown in FIG. 8. The biasing element 41 may include a compression spring, a leaf spring, a compressible material, a magnetic material having a magnetic interaction with a portion of the housing 22, such as the second end 32, or other similar biasing structure. Alternatively, the biasing element 41 may be a torsion spring disposed between a lower portion 46A of the binding plate 46 and a portion of the housing 22, such as the resistance plate 43. In this configuration, the biasing element 41 applies a torque to the binding plate 46. In yet another embodiment, the biasing element 41 may be disposed to impart a biasing force on a different or additional portion of the needle guard 24, such as disposed to impart a biasing force in a downwardly directed orientation on at least a portion of the base plate 90.

Figure 6:
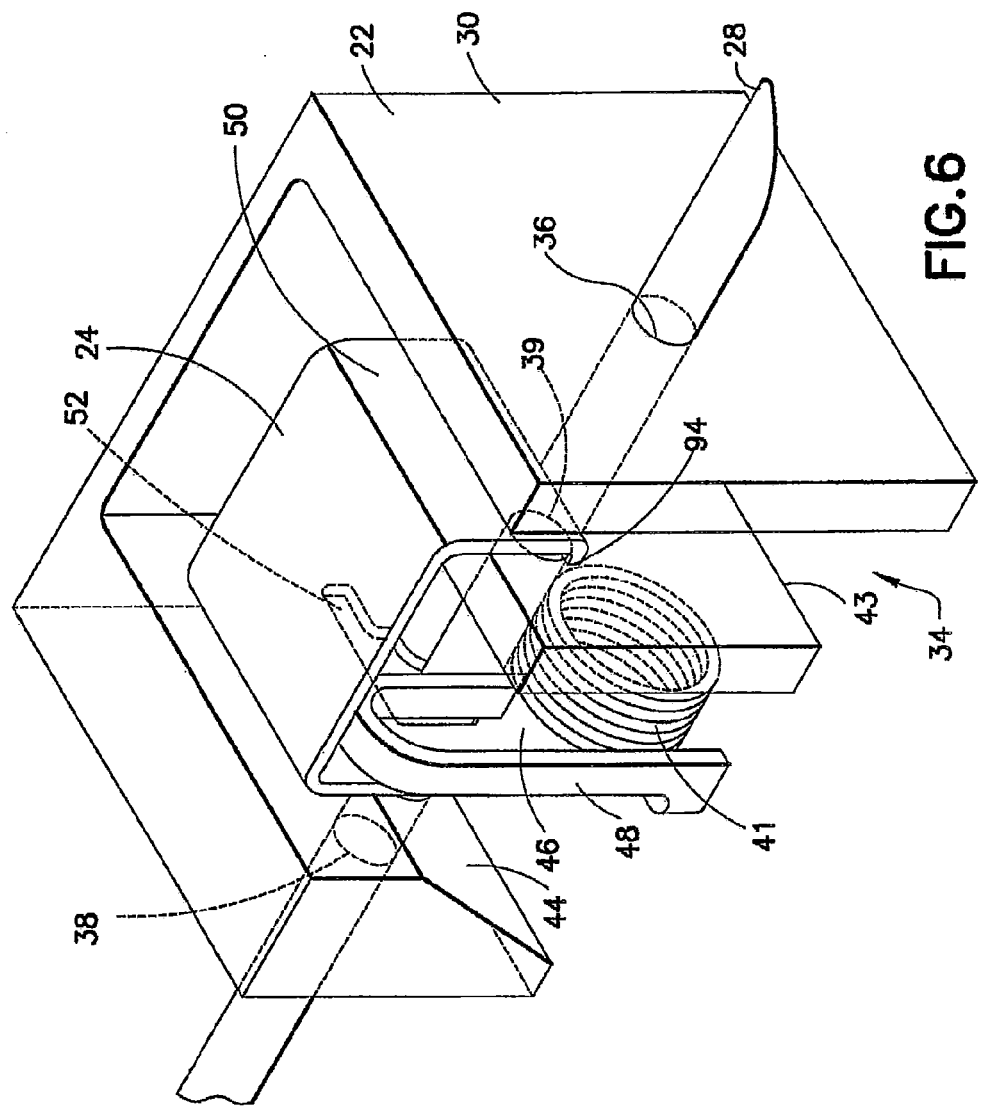
FIG. 6 is an assembled perspective view of the device of FIG. 1 in the restricted position having an outer cannula, an inner cannula, a needle guard, and a needle guard housing in accordance with an embodiment of the present invention.

The device 20 of FIG. 1 is shown in the assembled view in FIG. 6. It is noted herein that the device 20 shown in FIGS. 1 and 6 may include an exterior housing (not shown) which surrounds the device 20. As shown in FIG. 6, the needle guard 24 is disposed within the interior cavity 34 of the housing 22, and an outer needle cannula 28 is disposed through the first port 36, the second port 38, and the third port 39 of the housing 22. At least a portion of the multi-slot aperture is aligned with the first port 36, the second port 38, and the third port 39 along the axis A of the housing 22, such that the outer needle cannula 28 may also extend through at least a portion of the multi-slot aperture 52. In this orientation, the biasing member 48 is restrained by affixation to the binding plate 46 or by an interior portion of the housing 22, and biases the outer needle cannula 28 within the multi-slot aperture 52. The biasing element 41 is compressed between a portion of the resistance plate 43 and the binding plate 46. Also in this orientation, the contact surface 94 of the sensing arm 50 is adapted to contact a portion of the outer needle cannula 28. In one embodiment, the contact surface 94 of the sensing arm 50 is adapted to contact a portion of the outer needle cannula 28 at a location distal from the multi-slot aperture 52.

Figure 7:
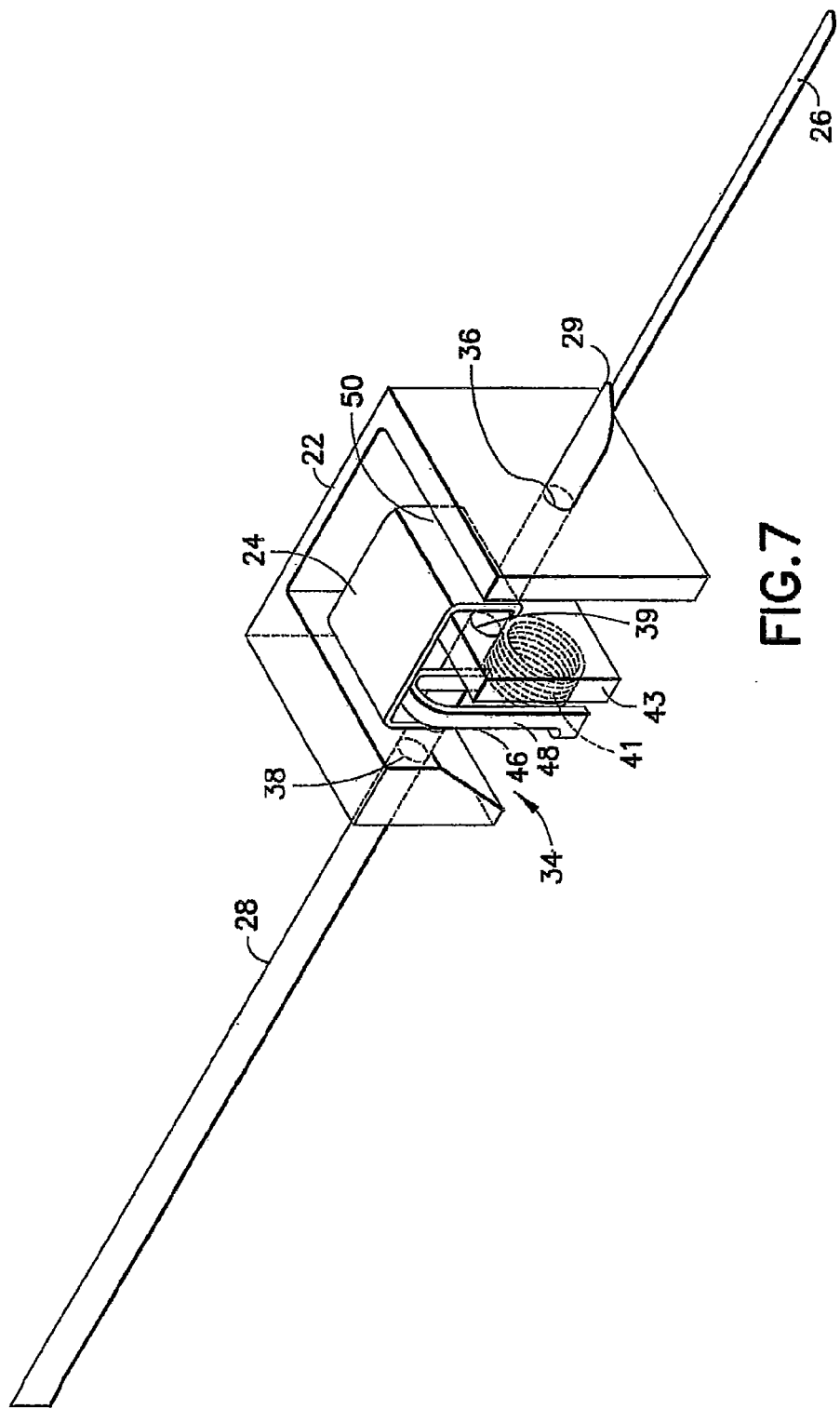
FIG. 7 is an assembled perspective view of the device of FIG. 6 in the restrained position having an outer cannula and inner cannula disposed therethrough in accordance with an embodiment of the present invention.
Figure 8A:
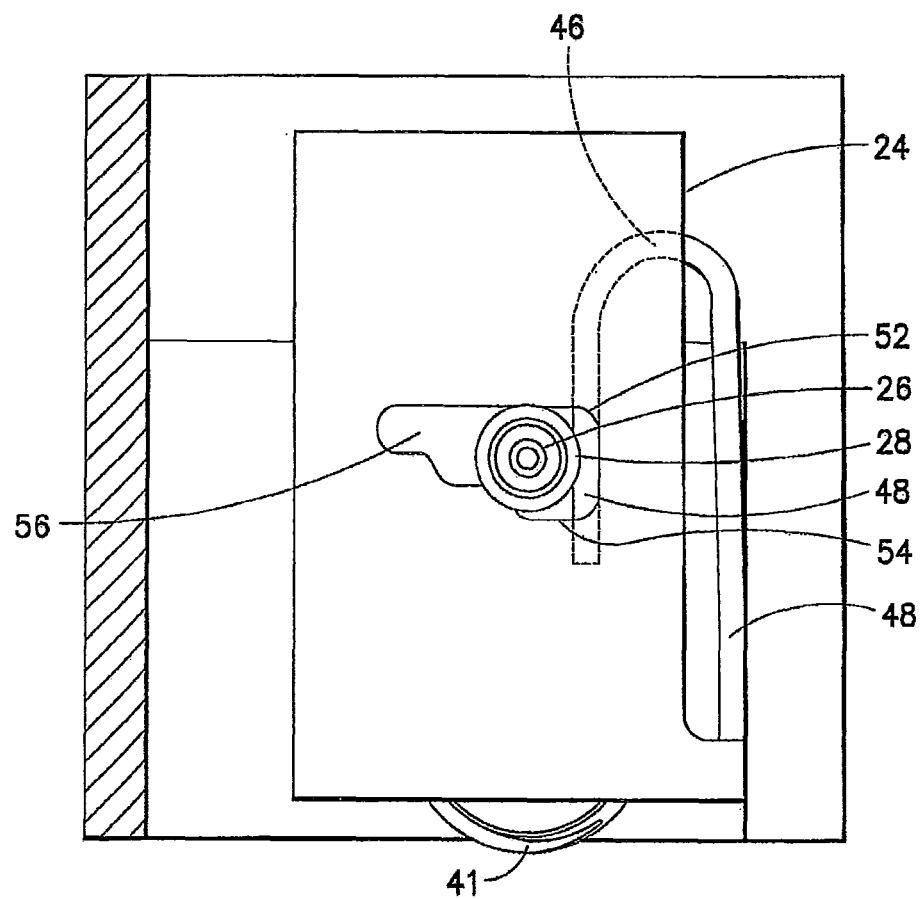
FIG. 8A is a cross-sectional view of the device of FIG. 7 taken along line 8A-8A of FIG. 8.
Figure 8B:
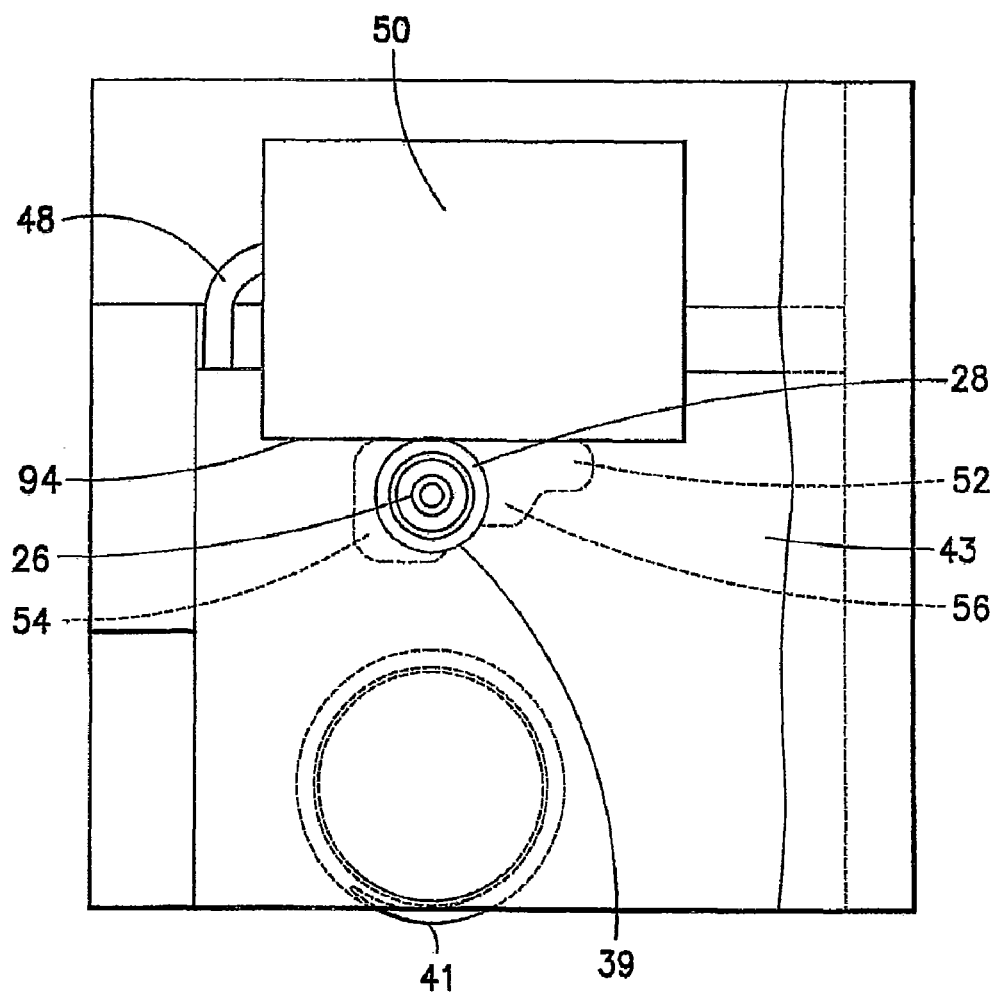
FIG. 8B is a front view of FIG. 7 viewing the front port of the housing.
Figure 10B:
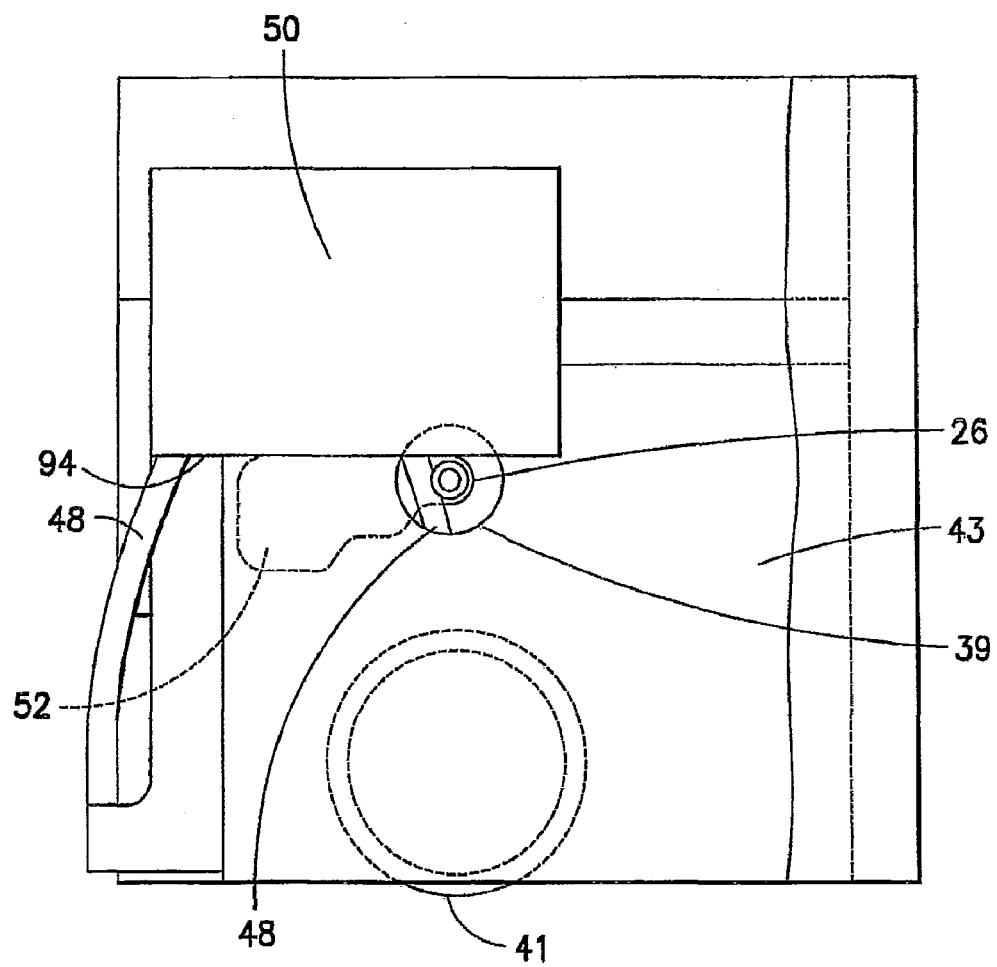
FIG. 10B is front view of the device of FIG. 9 viewing the front port of the housing.
Figure 11:
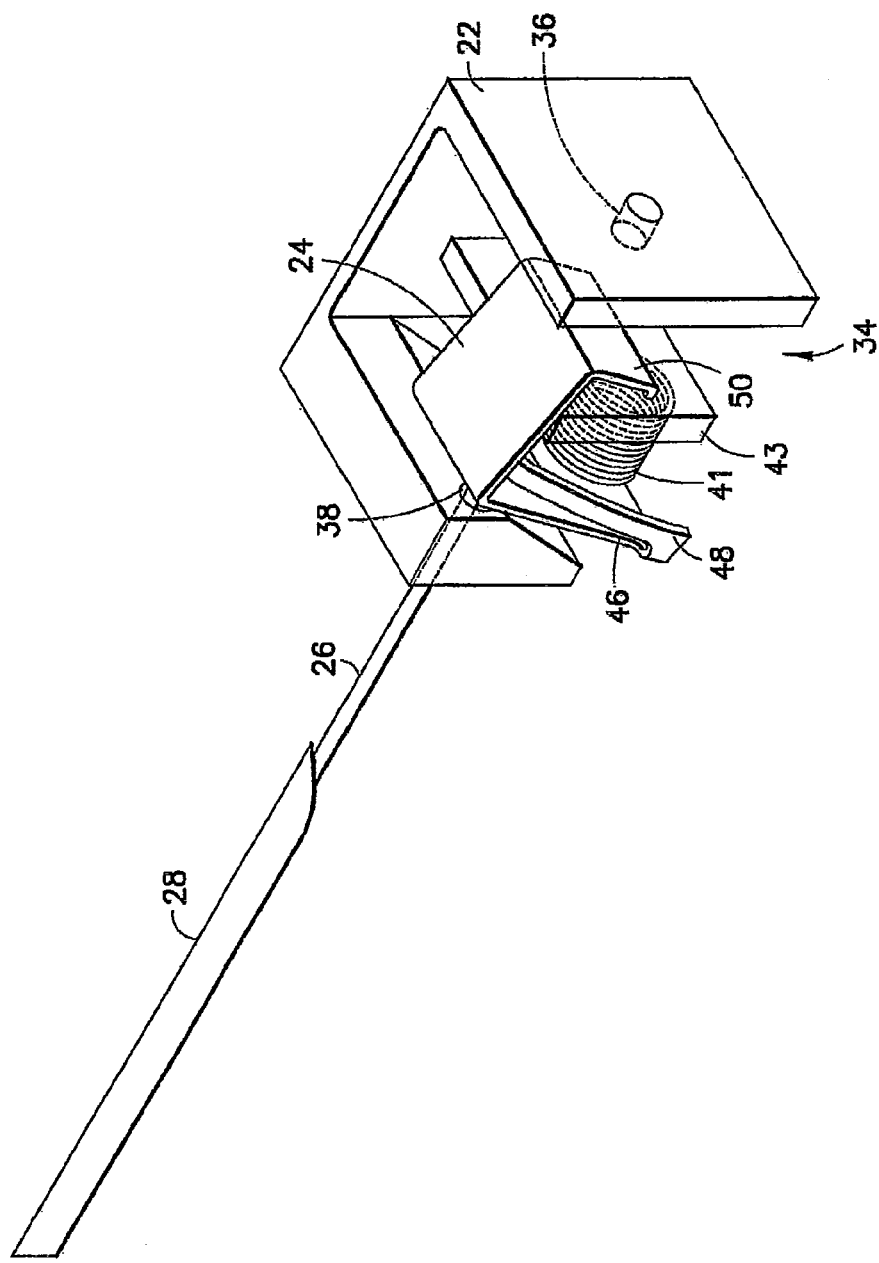
FIG. 11 is a perspective view of the device of FIG. 7 in the activated position having the inner cannula withdrawn from the first port in accordance with an embodiment of the present invention.
Figure 12:
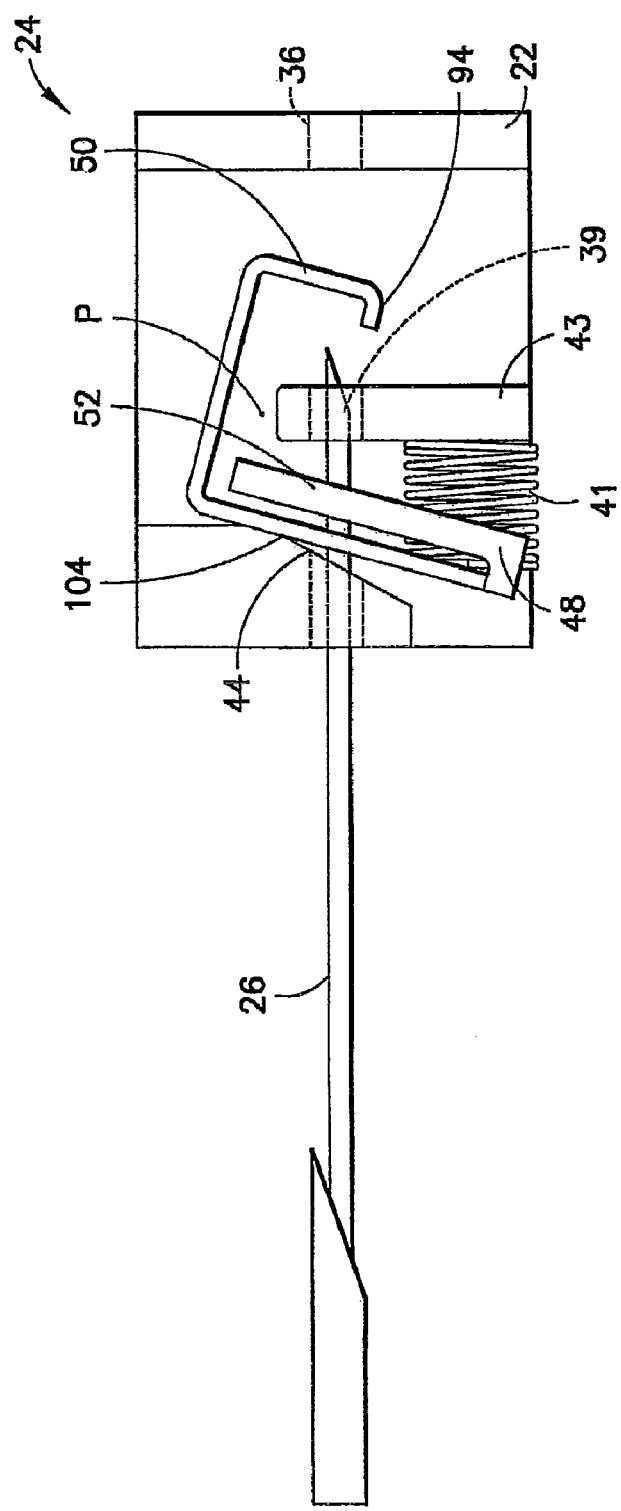
FIG. 12 is a side view of the device of FIG. 11 in the activated position.
Figure 12A:
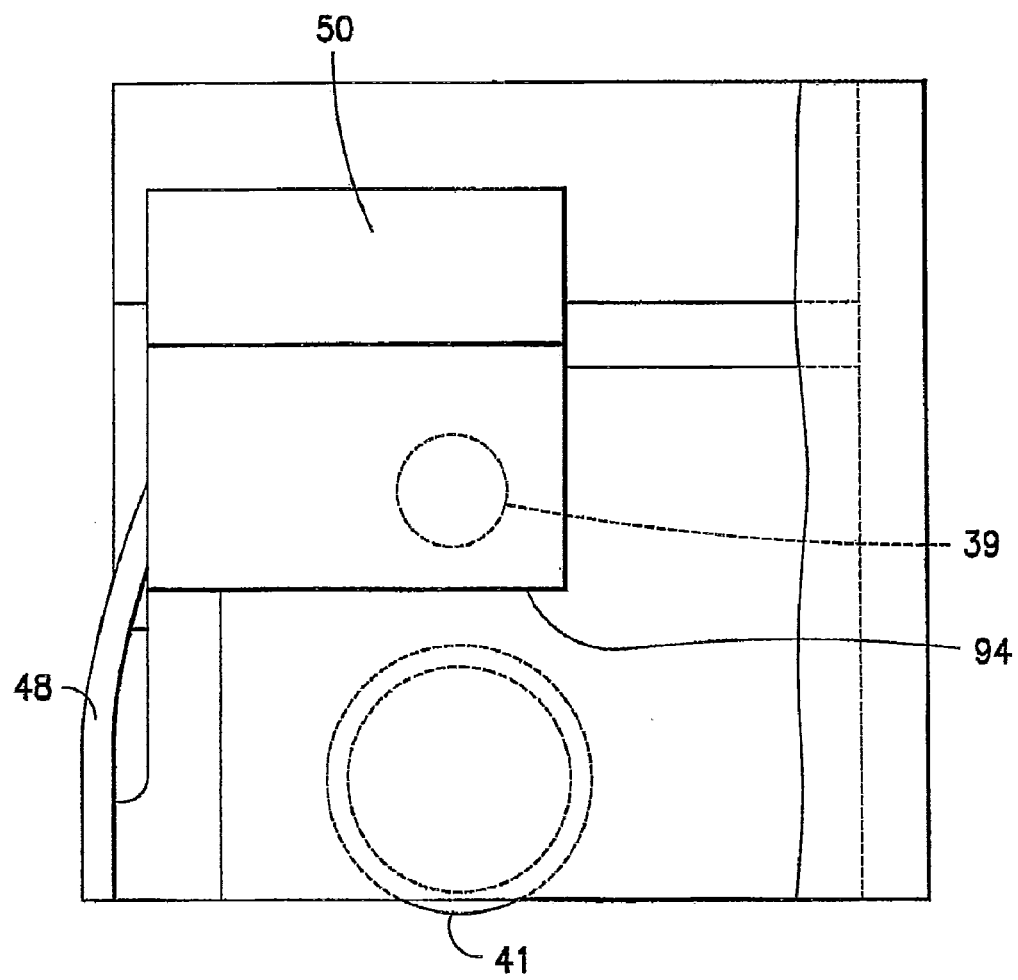
FIG. 12A is a front view of the device of FIG. 9 viewing the front port of the housing.

The needle guard 24 of the present invention is adapted to transition from a restrained position, shown in FIGS. 7-8B, to an intermediate restrained position, shown in FIGS. 9-10B, to an activated position, shown in FIGS. 11-12A. Optionally, the needle guard 24 may be adapted to transition from the restrained position, shown in FIGS. 7-8B, to the activated position, shown in FIGS. 11-12A, without first transitioning to an intermediate restrained position, shown in FIGS. 9-10B. In another embodiment, the needle guard 24 may be adapted to transition from the intermediate restrained position, shown in FIGS. 9-10B, to the activated position, shown in FIGS. 11-12A, without first transitioning from the restrained position, shown in FIGS. 7-8B, depending on the relevant cannula gauge employed therein. As shown in FIGS. 7-8B, the outer needle cannula 28 is disposed through the first region 54 of the multi-slot aperture 52, shown in FIG. 3, and through both first port 36 and the second port 38, and the third port 39 of the resistance plate 43 of the housing 22. The inner needle cannula 26 may be disposed within the outer needle cannula 28. The needle guard 24 of the present invention is intended to be disposed on at least a portion of an outer needle cannula 28, in a restrained position, during the performance of a standard medical procedure. In the restrained position, the needle tip 29 of the outer needle cannula 28 may be generally exposed. The contact surface 94 of the sensing arm 50 contacts the needle cannula surface 100. As shown in FIGS. 8A and 8B, the biasing member 48 biases the outer needle cannula 28 (with the inner needle cannula 26 nested therein) within the first region 54 of the multi-slot aperture 52. As the multi-slot aperture 52 is dimensioned to allow the outer needle cannula 28 to be disposed within the first region 54, but not the second region 56, the biasing member 48 creates a continuous pressure of the cannula surface 100 against a portion of the multi-slot aperture 52 separating the first region 54 and the second region 56. Referring again to FIGS. 7-8B, the biasing element 41, disposed between the resistance plate 43 and the needle guard 24 biases the lower portion 46A of the binding plate 46 toward the second end 32 of the housing 22. The needle guard 24 is held in a stationary position from the corresponding force applied by the contact between the outer surface 100 of the outer needle cannula 28 and the contact surface 94 of the sensing arm 50.

After or during a medical procedure, it may be desirable to advance the needle guard 24 over the outer needle cannula 28 onto an inner needle cannula 28. Optionally, it may be desirable to fully withdraw the outer needle cannula 28 or to advance the needle guard 24 over the needle tip 29 of the outer needle cannula 28 along the inner needle cannula 26. In one embodiment, the advancement of the needle guard 24 can occur while the needle tip 31 of the inner needle cannula 26 is inside the patient. Alternatively, advancement of the needle guard 24 can occur once the needle tip 31 on the inner cannula 26 has been removed from the patient.

As shown in FIGS. 9-10B, as the needle guard 24 is advanced over the needle tip 29 of the outer needle cannula 28, the contact surface 94 of the sensing arm 50 drops toward the through-axis T of the multi-slot aperture 52, shown in FIG. 1, until contact with the needle cannula surface 102 of the inner needle cannula 26 is made. As shown in FIGS. 9-10B, once the needle guard 24 is transitioned from an outer cannula 28 to an inner cannula 26, the needle guard is in the intermediate restrained position. Once the larger diameter outer needle cannula 28 is removed from the multi-slot aperture 52, the biasing member 48 advances the inner needle cannula 26 into the smaller dimensioned second region 56 of the multi-slot aperture 52, as shown in FIG. 10A. If sizing of the first region 54, second region 56 and third region 62 in relation to the cannula 28 permit, the cannula 28 may pass from the second region 56 into the third region 62. In a further configuration, the outer cannula 28 may be initially disposed within the second region 56, and the inner cannula 26 nested therein may become disposed within the third region 62 once the outer cannula 28 is removed thereover. The needle guard 24 is then held in a stationary position from the corresponding force applied by the contact between the outer surface 102 of the inner needle cannula 26 and the contact surface 94 of the sensing arm 50. As shown in FIGS. 10A and 10B, the biasing member 48 biases the inner needle cannula 26 within a second region 56 of the multi-slot aperture 52. As shown in FIG. 10B, a portion of the biasing member 48 is visible through the third port 39 of the resistance plate 43.

As shown in FIGS. 11-12A, once the medical procedure is complete, the needle guard may be advanced over the needle tip 31 of the inner needle cannula 26. The sensing arm 50 of the needle guard 24 is positionable for restricting movement of the needle cannula, such as the inner needle cannula 26. In the restrained or intermediate restrained position, shown in FIGS. 7-10B, the sensing arm 50 is restrained from restricting movement of the inner needle cannula 26 by contact between the contact surface 94 and the needle cannula surface 102. As shown in FIGS. 11-12A, as the inner needle cannula 26 is pulled in a proximal direction, the needle tip 31 passes beyond the sensing arm 50 and contact between the contact surface 94 and the needle cannula surface 102 is interrupted.

Once contact between the needle cannula surface 102 and the contact surface 94 of the sensing arm 50 is interrupted, the sensing arm 50 drops at least partially below the through-axis T of the multi-slot aperture 52 and the sensing arm 50, the binding plate 46 and the biasing member 48 pivot within the interior cavity 34 of the housing 22 about a pivot axis. Once the reaction force caused by contact between the contact surface 94 of the sensing arm 50 and the needle cannula 28 is disrupted, the biasing force of the biasing member 41 forces the lower portion 46A of the binding plate 46 away from the resistance plate 43. In another embodiment, the biasing member 41 forces the lower portion 46A of the binding plate 46 toward the rearward portion 104 of the housing 22, such as about pivot P, such that the binding plate 46 becomes tilted with respect to its initial position, shown in FIGS. 7-9B.

This pivoting motion advances the sensing arm 50, particularly the engagement plate 92, in a downward direction toward the through axis T of the housing 22 and occludes the first port 36 to restrict the movement of the inner needle cannula 26 in the distal direction. In one embodiment, the binding plate 46 tilts until both the top and bottom edge of the multi-slot aperture 52 make contact with the corresponding top and bottom of the inner cannula 26 (or outer cannula 28). This tilt angle is typically from about 5° to about 10°, depending on the dimensional relationship between the cannula 26, 28 and the multi-slot aperture 52. The tilt of the binding plate 46 is observed once transitioned to the initial activated position. If additional force is applied to a needle cannula 26 disposed within the binding plate 46 in a direction substantially proximal to the needle guard 24, the tilt of the binding plate 46 may be increased until a rearward portion 104 of the binding plate 46 may be aligned with or contacts at least a portion of the angled interior surface 44 of the housing 22, or optionally another portion of the housing 22, at this maximum tilt, when the needle guard 24 is heavily loaded, such as during the application of force in a proximal direction after transition to the activated position. The frictional resistance between the inner cannula 26 and the tilted binding plate 46 prevents removal of the inner cannula 26 from the needle guard 24 in the proximal direction absent intentionally applied malicious force. Optionally, a portion of the inner cannula 26 may be deformed against a portion of the binding plate 46 during transition to the activated position and/or during application of applied force on the needle cannula 26 in the proximal direction after transition to the activated position.

Accordingly, the locking mechanism of the needle guard 24 of the present invention is capable of restraining the tip of a needle in a distal direction by transitioning the sensing arm 50 from the restrained position to the activated position. The locking mechanism of the needle guard 24 of the present invention is also capable of restraining the tip of a needle in the proximal direction by effectively binding and jamming the tilted binding plate 46 against the needle cannula 26.

The needle guard 24 of the present invention can effectively "jump" from a larger diameter outer needle cannula 28 to a smaller diameter inner needle cannula 26, without transitioning from the restrained position, as shown in FIGS. 7-10B, to the activated position, shown in FIGS. 11-12A. When the needle guard 24 is advanced over the needle tip 29 of the outer needle cannula 28, the sensing arm 50 contacts the needle cannula surface 102 of the inner needle cannula 26, thereby preventing transition to the activated position. In another embodiment, it is contemplated herein that multiple nested needle cannulas, such as three, four, or five needle cannulas, may be used with the needle guard of the present invention. Alternatively, the needle guard 24 of the present invention may be used with a single needle cannula and/or solid stylet.

A beneficial aspect of producing a needle guard 24 adapted to receive a plurality of varying cannula gauges is a significant decrease in the associated production expenses, as the amount of tooling and fabrication inventory is decreased. By utilizing a needle guard 24 that accommodates many different needle or cannula gauges, the number of different types of needle guards that are needed is significantly reduced.

Figure 13:
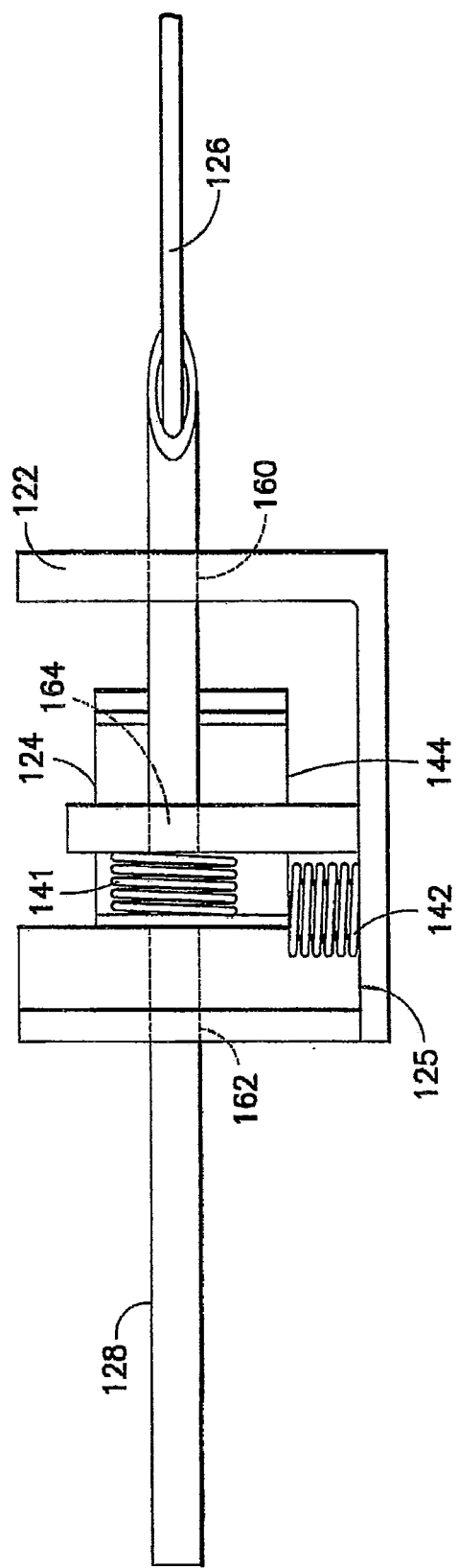
FIG. 13 is a bottom view of an alternative device having a second biasing element in the retracted position in accordance with an embodiment of the present invention.
Figure 13A:
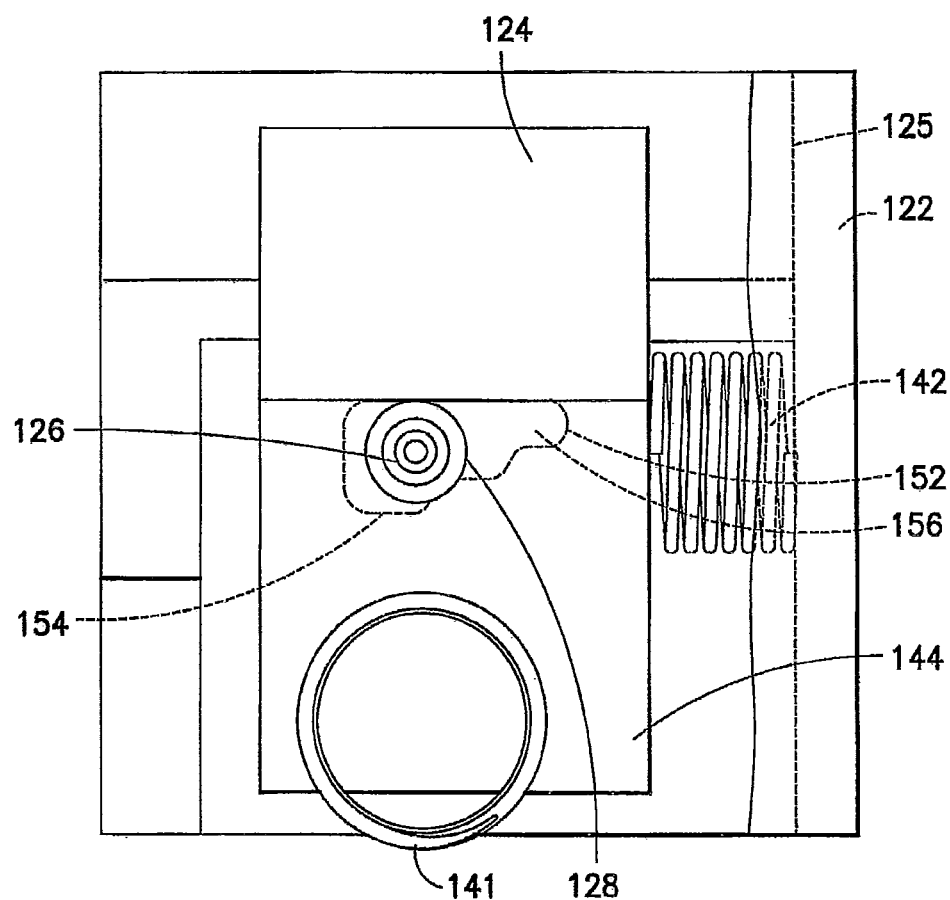
FIG. 13A is a front view of the device of FIG. 13.
Figure 13B:
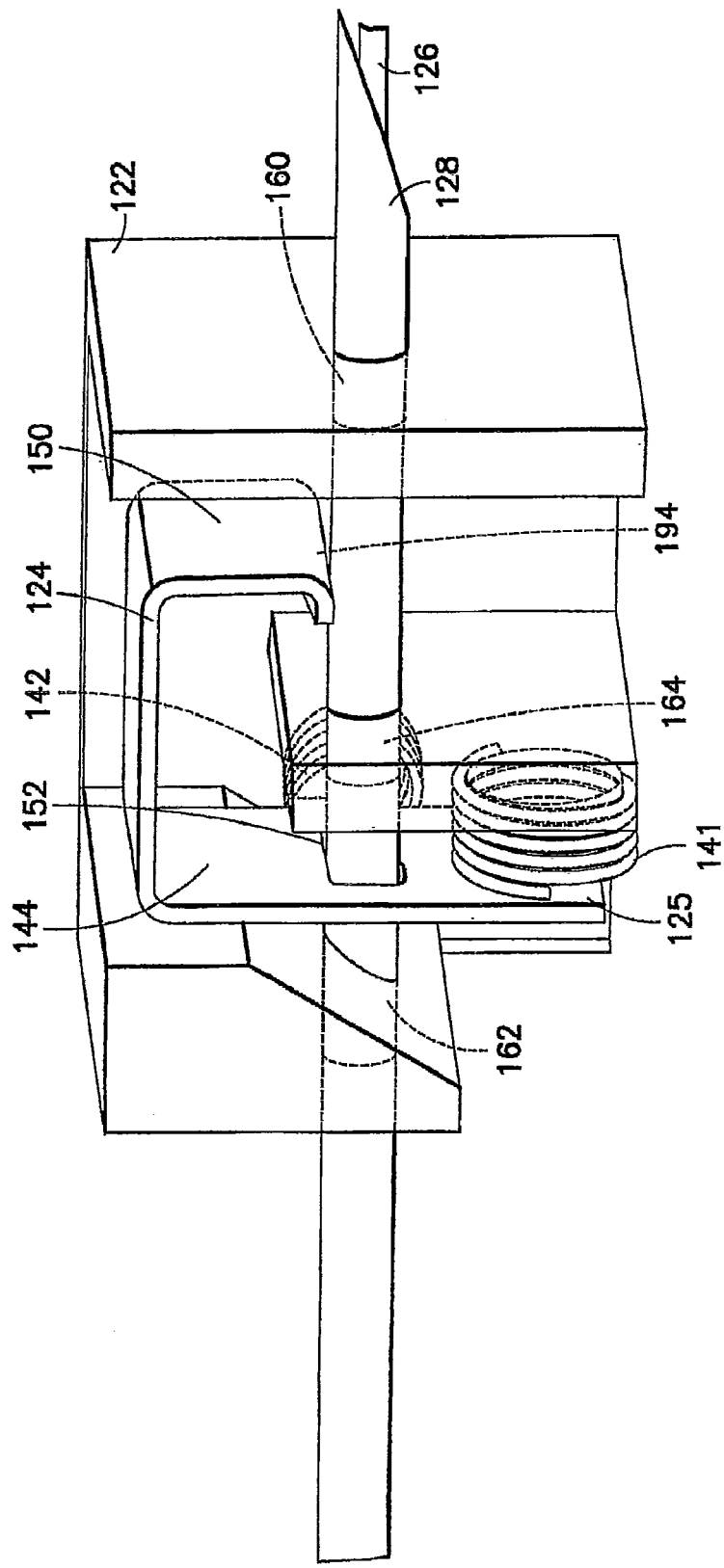
FIG. 13B is a perspective view of the device of FIG. 13.

In an alternative embodiment of the present invention, as shown in FIGS. 13-13B, the needle guard 124 is similarly described above and disposed within an interior of the housing 122. In addition to biasing element 141, described above with reference to element 41, a second biasing element 142 is disposed between a portion of the interior of the housing 122 and the needle guard 124. The second biasing element 142 may include a compression spring, a leaf spring, a compressible material, a magnetic material having a magnetic interaction with a portion of the housing 122, or other similar biasing structure.

In one embodiment, the second biasing element 142 is disposed between an interior wall 125 of the housing 122 and a portion of the binding plate 144 having a multi-slot aperture 152 disposed therein. A nested outer cannula 128 and inner cannula 126 may be disposed through a first port 160, a second port 162 and a third port 164 of the housing. The outer cannula 128 may also be disposed within a portion of the multi-slot aperture 152, such as through a first region 154. The second biasing element 142 biases the binding plate 144, such as a portion of the multi-slot aperture 152 against a portion of the outer cannula 128. In one embodiment, the outer gauge of the outer cannula 128 may contact the multi-slot aperture 152 between a first region 154 and a second region 156. The second biasing element 142 is held in a biased state by the physical interaction between the outer cannula 128 and the second region 156 of the multi-slot aperture 152, which has a dimension smaller than the outer dimension of the outer cannula 128. In one configuration, the first biasing element biases the binding plate 144 in the distal to proximal direction along the longitudinal axis A, shown in FIG. 1, to bias the binding plate 144 toward a tilted position. As discussed above, the interaction of the contact surface 194 of the sensing arm 150 and the outer cannula 128 prevents the first biasing element 141 from tilting the binding plate 144. In another embodiment, the second biasing element 142 biases the binding plate 144 in a direction substantially perpendicular to the bias of the first binding element 141. In one embodiment, the second biasing element 142 biases the binding plate 144 in a direction that is substantially aligned with the multi-slot aperture 152 such that a portion of the multi-slot aperture 152 engages the outer cannula 128 disposed therein.

Figure 14:
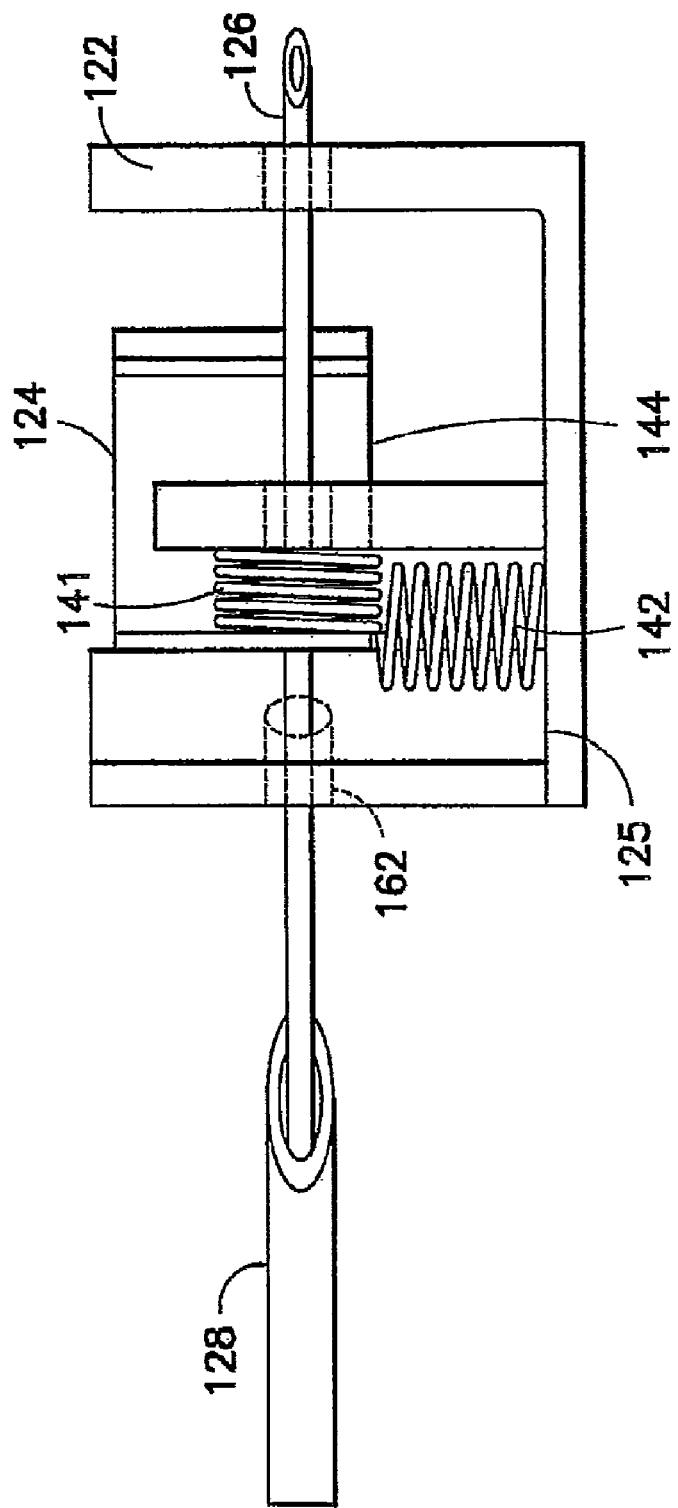
FIG. 14 is a bottom view of the device of FIG. 13 in the intermediate restrained position.
Figure 14A:
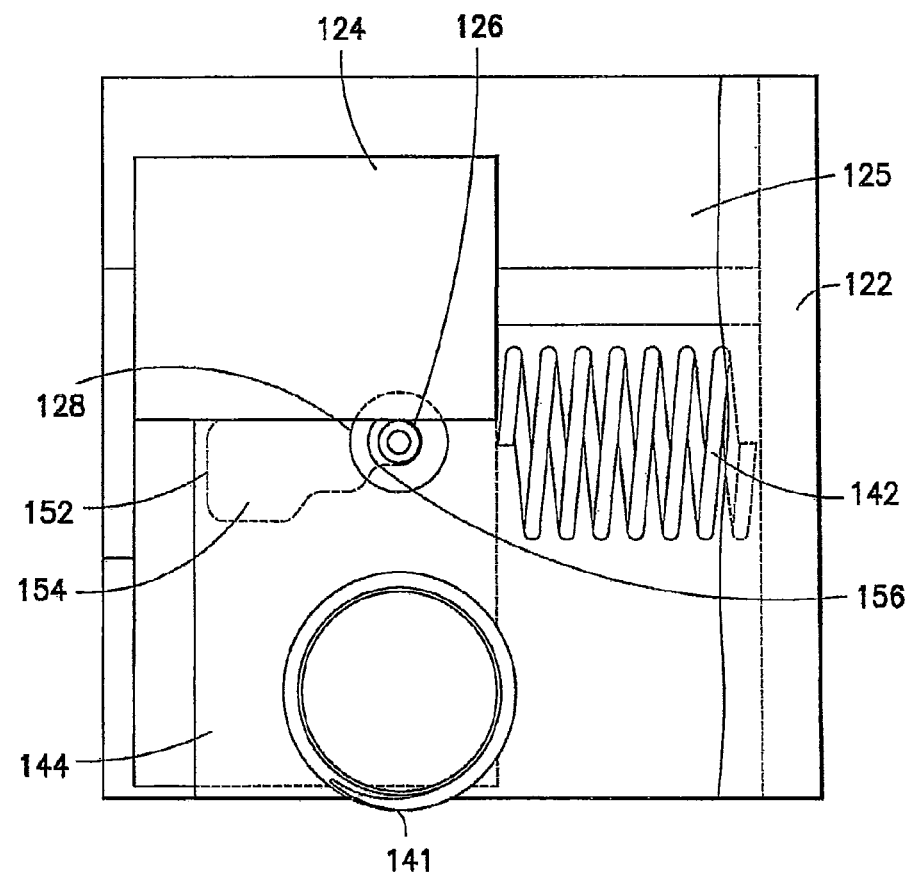
FIG. 14A is a front view of the device of FIG. 14.
Figure 14B:
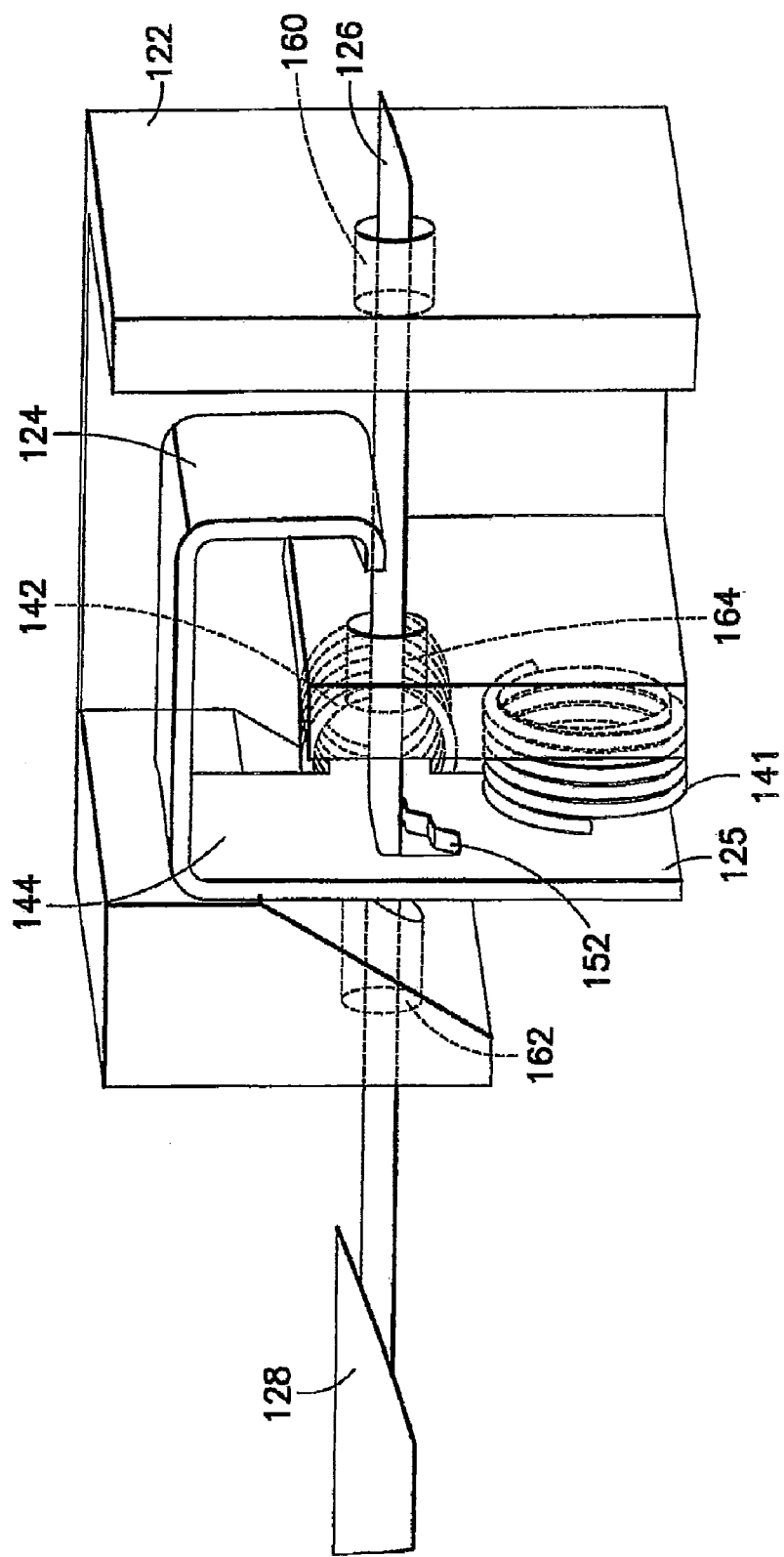
FIG. 14B is a perspective view of the device of FIG. 14.

As shown in FIGS. 14-14B, when the outer cannula 128 is removed from the housing 122, or removed from the third port 164 of the housing 122, the inner cannula 126 having a smaller diameter than the outer cannula 128 is disposed within the multi-slot aperture 152, as described herein. In this configuration, the second biasing element 142 advances the binding plate 144, specifically the multi-slot aperture 152 of the binding plate 144 away from the interior wall 125 of the housing 122 in the direction of the bias of the second biasing element 142. As the outer diameter of the inner cannula 126 is smaller than the outer diameter of the outer cannula 128, the multi-slot aperture 152 is advanced such that the inner cannula is disposed within a second region 156. As shown in FIGS. 14-14B, the entire needle guard 124 is shifted with respect to the housing 122 in the intermediate restricted position, as compared to the initial restricted position, shown in FIGS. 13-13B.

Figure 15:
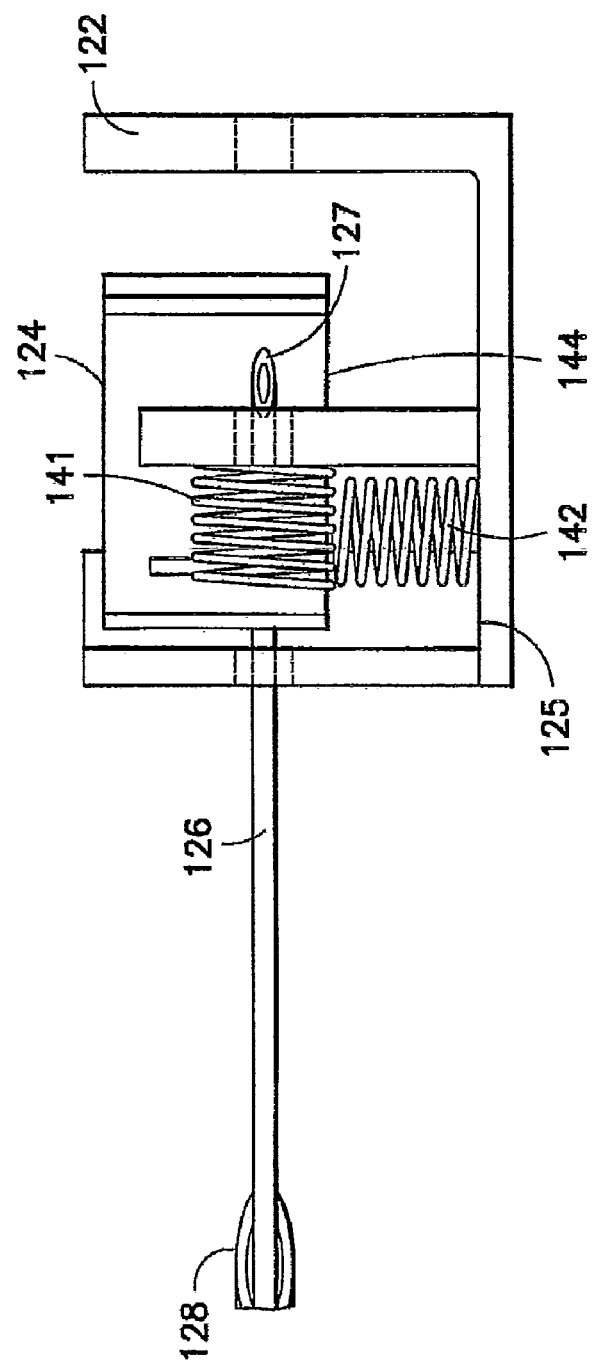
FIG. 15 is a bottom view of the device of FIG. 13 in the activated position.
Figure 15A:
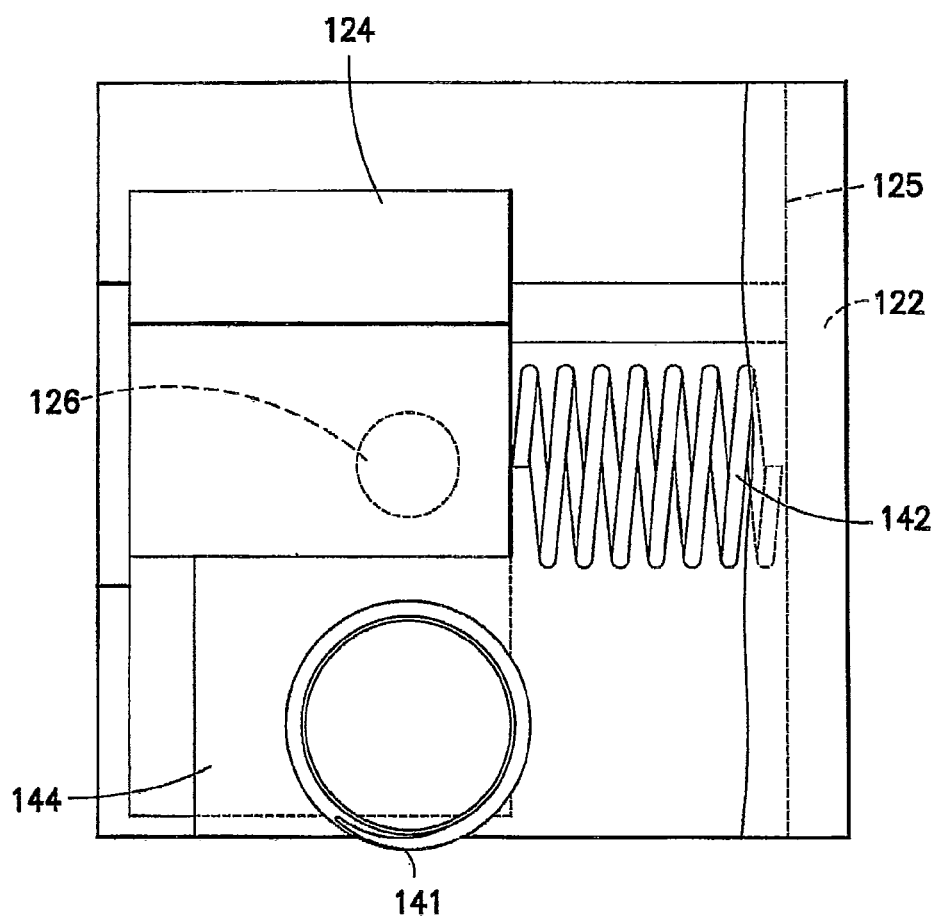
FIG. 15A is a front view of the device of FIG. 15.
Figure 15B:
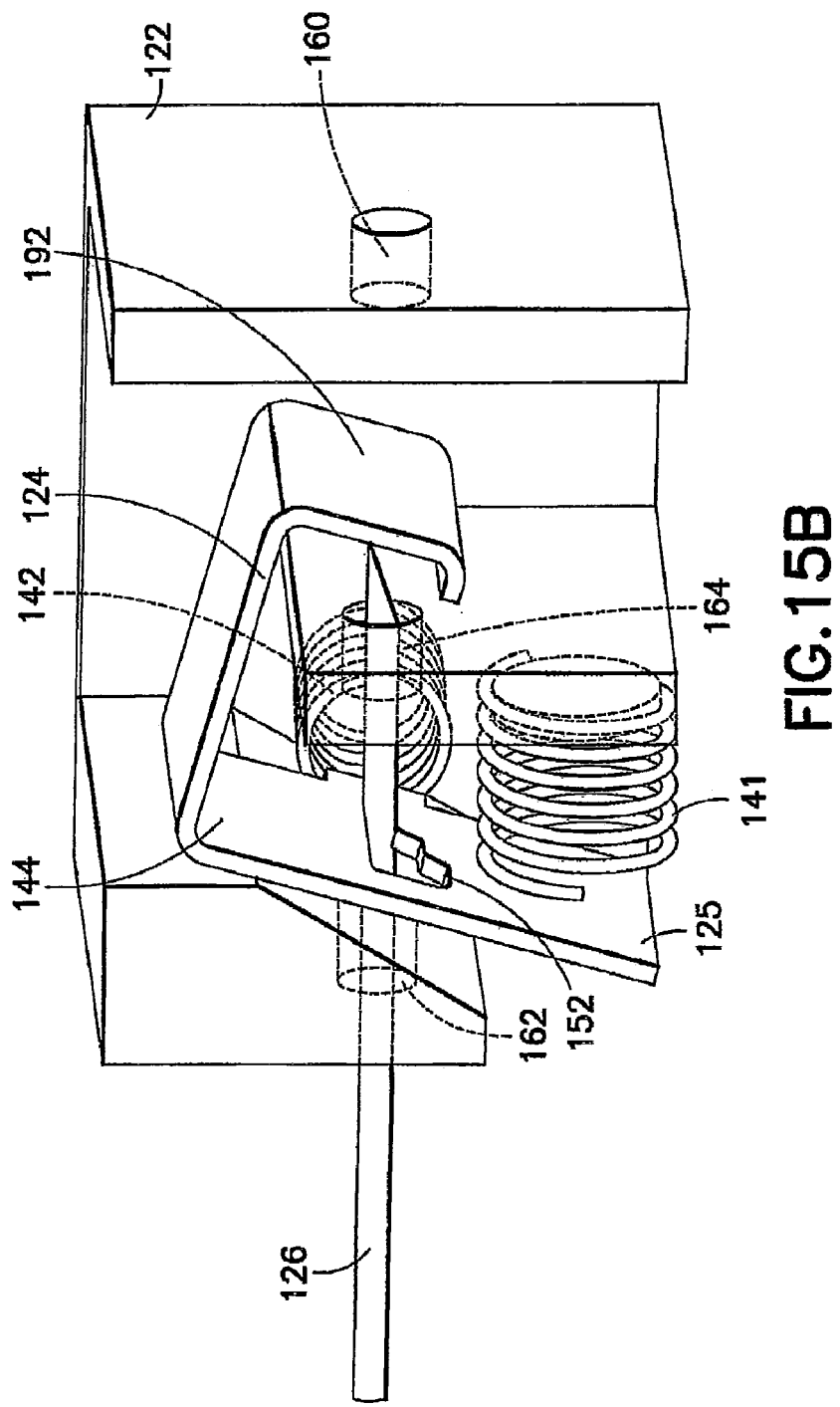
FIG. 15B is a perspective view of the device of FIG. 15.

As shown in FIGS. 15-15B, once the needle tip 127 of the inner cannula 126 is passed within the interior of the housing 122, the needle guard 124 tilts forward and the engagement plate 192 drops downward to prevent distal movement of the needle tip, as similarly described herein. Simultaneously, the first biasing element 141 tilts the binding plate 144 thereby binding and jamming the inner cannula 126, as also similarly described herein.

While the present invention is described with reference to several distinct embodiments of a needle guard and method of use, those skilled in the art may make modifications and alterations without departing from the scope and spirit. Accordingly, the above detailed description is intended to be illustrative rather than restrictive.

What is claimed is:

1. A needle guard, comprising:
   a binding plate defining a multi-slot aperture, the multi-slot aperture adapted to receive a needle cannula therethrough;
   a biasing member biasing the needle cannula within the multi-slot aperture; and
   a sensing arm connected to the binding plate adapted to contact a portion of the needle cannula, and positionable for restricting movement of the needle cannula in a distal direction,
   wherein the multi-slot aperture comprises a first region having a first dimension, and a second region having a second dimension, the second dimension being smaller than the first dimension, and wherein the biasing member is adapted to advance the needle cannula within the multi-slot aperture from the first region to the second region, wherein upon advancement of the needle cannula within the multi-slot aperture by the biasing member, the binding plate is adapted to tilt and contact the needle cannula, thereby preventing movement of the needle cannula in a proximal direction.

2. The needle guard of claim 1, wherein the biasing member is disposed adjacent the multi-slot aperture.

3. The needle guard of claim 1, wherein the biasing member is initially positioned adjacent the first region of the multi-slot aperture.

4. The needle guard of claim 1, wherein the biasing member is adapted to apply a biasing force adjacent the multi-slot aperture in a direction that is substantially perpendicular to a through-axis of the multi-slot aperture.

5. The needle guard of claim 1, wherein the sensing arm further comprises a transverse barrier.

6. The needle guard of claim 5, wherein the transverse barrier comprises:
   a base plate connected to the binding plate and extending in a distal direction from the binding plate, and
   an engagement plate connected to, and extending from, the base plate in a direction toward a through-axis of the multi-slot aperture, wherein the engagement plate comprises a contact surface for contacting a portion of the needle cannula at a location distal from the multi-slot aperture.

7. The needle guard of claim 6, wherein the contact surface comprises an angled restraining lip extending toward the multi-slot aperture.

8. The needle guard of claim 1, further comprising a biasing element biasing the binding plate in a distal to proximal direction to bias the binding plate toward a tilted position.

9. The needle guard of claim 8, further comprising a second biasing element biasing the binding plate in a direction substantially aligned with the multi-slot aperture.

10. The needle guard of claim 1, wherein the biasing member is adapted to advance the needle cannula within the multi-slot aperture from the first region to the second region in a direction perpendicular to a longitudinal axis of the needle cannula.

11. A needle guard, comprising:
    a housing, defining an interior, and having a first port and a second port extending therethrough and aligned along an axis of the housing; and
    a locking mechanism disposed within the interior of the housing, the locking mechanism comprising:
       a binding plate defining a multi-slot aperture, at least a portion of the multi-slot aperture aligned with the first port and the second port along the axis of the housing, wherein the first port, the second port, and the multi-slot aperture are adapted to receive a needle cannula therethrough,
       a biasing member for biasing the needle cannula within the aperture, and
       a sensing arm connected to the binding plate adapted to contact the needle cannula, and positionable for restricting movement of the needle cannula in a distal direction,
    wherein the multi-slot aperture comprises a first region having a first dimension, and a second region having a second dimension, the second dimension being smaller than the first dimension, and wherein the biasing member is adapted to advance the needle cannula within the multi-slot aperture from the first region to the second region, wherein upon advancement of the needle cannula within the multi-slot aperture by the biasing member, the binding plate is adapted to tilt and contact the needle cannula, thereby preventing movement of the needle cannula in a proximal direction.

12. The needle guard of claim 11, wherein the biasing member is disposed adjacent the multi-slot aperture.

13. The needle guard of claim 11, wherein the interior of the housing comprises an angled interior surface for accommodating a portion of the binding plate thereagainst.

14. The needle guard of claim 11, wherein the biasing member is adapted to apply a biasing force adjacent the multi-slot aperture in a direction that is substantially perpendicular to a through-axis of the multi-slot aperture.

15. The needle guard of claim 11, wherein the sensing arm further comprises a transverse barrier.

16. The needle guard of claim 15, wherein the transverse barrier comprises:
    a base plate connected to the binding plate and extending in a distal direction from the binding plate, and
    an engagement plate connected to, and extending from, the base plate in a direction toward a through-axis of the multi-slot aperture, wherein the engagement plate comprises a contact surface for contacting a portion of the needle cannula at a location distal from the multi-slot aperture.

17. The needle guard of claim 16, wherein the contact surface comprises an angled restraining lip extending toward the multi-slot aperture.

18. The needle guard of claim 11, wherein the locking mechanism is adapted to pivot within the interior of the housing about a pivoting axis to position the sensing arm to restrict movement of the needle cannula.

19. The needle guard of claim 11, further comprising a biasing element biasing the binding plate in a distal to proximal direction to bias the binding plate toward a tilted position.

20. The needle guard of claim 19, further comprising a second biasing element biasing the binding plate in a direction substantially aligned with the multi-slot aperture.

21. The needle guard of claim 11, wherein the biasing member is adapted to advance the needle cannula within the multi-slot aperture from the first region to the second region in a direction perpendicular to a longitudinal axis of the needle cannula.

22. A device, comprising:
a needle cannula having a cannula tip;
a housing disposed about a portion of the needle cannula, defining an interior, and having a first port and a second port extending therethrough and aligned along an axis of the housing; and
a locking mechanism disposed within the interior of the housing, the locking mechanism comprising:
a binding plate defining a multi-slot aperture, at least a portion of the multi-slot aperture aligned with the first port and the second port along the axis of the housing, wherein the first port, the second port, and the multi-slot aperture are adapted to receive the needle cannula therethrough;
a biasing member for biasing the needle cannula within the aperture, the biasing member positionable for restricting movement of the needle cannula in a distal direction; and
a transverse barrier connected to the binding plate adapted to contact a portion of the needle cannula, and positionable for restricting movement of the needle cannula in a proximal direction, wherein upon advancement of the needle cannula within the multi-slot aperture by the biasing member, the transverse barrier and the binding plate are adapted to tilt and contact the needle to prevent movement of the needle cannula in the proximal direction
wherein the multi-slot aperture comprises a first region having a first dimension, and a second region having a second dimension, the second dimension being smaller than the first dimension, and wherein the biasing member is adapted to advance the needle cannula within the multi-slot aperture from the first region to the second region.

23. The device of claim 22, wherein the biasing member is disposed adjacent the multi-slot aperture.

24. The device of claim 22, wherein the transverse barrier comprises:
a base plate connected to the binding plate and extending in a distal direction from the binding plate, and
an engagement plate connected to, and extending from, the base plate in a direction toward a through-axis of the multi-slot aperture, wherein the engagement plate comprises a contact surface for contacting a portion of the needle cannula at a location distal from the multi-slot aperture.

25. The device of claim 24, wherein the contact surface comprises an angled restraining lip extending toward the multi-slot aperture in a direction that is substantially parallel to the through-axis of the multi-slot aperture.

26. The device of claim 22, wherein the transverse barrier comprises a contact surface, and the transverse barrier is restrained from restricting movement of the needle cannula by contact between the contact surface and the needle cannula.

27. The device of claim 26, wherein the transverse barrier is positioned to restrict movement of the needle cannula in the distal direction when contact between the contact surface and the needle cannula is interrupted.

28. The device of claim 22, wherein the locking mechanism is adapted to pivot within the interior of the housing about a pivoting axis to position the sensing arm to restrict movement of the needle cannula.

29. The device of claim 28, wherein the locking mechanism is adapted to pivot about the pivoting axis when contact between a contact surface of the sensing arm and the needle cannula is interrupted.

30. The device of claim 22, wherein the interior of the housing comprises an angled interior surface for accommodating a portion of the binding plate thereagainst.

31. The device of claim 22, wherein the biasing member is adapted to bias the needle cannula against the first port and the second port of the housing in a restrained position, and against at least a portion of the multi-slot aperture in an activated position.

32. The device of claim 22, further comprising a biasing element biasing the binding plate in a distal to proximal direction to bias the binding plate toward a tilted position.

33. The device of claim 32, further comprising a second biasing element biasing the binding plate in a direction substantially aligned with the multi-slot aperture.

34. The device of claim 22, wherein the biasing member is adapted to advance the needle cannula within the multi-slot aperture from the first region to the second region in a direction perpendicular to a longitudinal axis of the needle cannula.

35. A method of actuating a needle guard, comprising the steps of:
providing a needle guard disposed about at least a portion of a needle cannula, the needle guard comprising:
a housing, defining an interior, and having a first port and a second port extending therethrough and aligned along an axis of the housing; and
a locking mechanism disposed within the interior of the housing, the locking mechanism comprising:
a binding plate defining a multi-slot aperture, at least a portion of the multi-slot aperture aligned with the first port and the second port along the axis of the housing, wherein the first port, the second port, and the multi-slot aperture are adapted to receive the needle cannula therethrough;
a biasing member for biasing the needle cannula within the aperture;
a sensing arm connected to the binding plate and comprising a contact surface, wherein the sensing arm is adapted to transition from a restrained position in which the contact surface contacts a portion of the needle cannula, to an activated position in which the sensing arm restricts movement of the needle cannula in a distal direction; and
at least one biasing element for biasing the binding plate in a distal to proximal direction, wherein the multi-slot aperture comprises a first region having a first dimension, and a second region having a second dimension, the second dimension being smaller than the first dimension, and wherein the biasing member is adapted to advance the needle cannula within the multi-slot aperture from the first region to the second region, wherein upon advancement of the needle cannula within the multi-slot aperture by the biasing member, the binding plate is adapted to tilt and contact the needle cannula, thereby preventing movement of the needle cannula in a proximal direction; and transitioning the sensing arm from the restrained position to the activated position by interrupting contact between the contact surface and the needle cannula.

36. The method of claim 35, wherein the biasing member is adapted to advance the needle cannula within the multi-slot aperture from the first region to the second region in a direction perpendicular to a longitudinal axis of the needle cannula.

* * * * *